(12) United States Patent
Shiraishi et al.

(10) Patent No.: US 9,974,507 B2
(45) Date of Patent: May 22, 2018

(54) X-RAY DIAGNOSIS APPARATUS INCLUDING PROCESSING CIRCUITRY TO SELECT A ROADMAP IMAGE BASED ON PIXEL VALUES

(71) Applicant: Toshiba Medical Systems Corporation, Otawara-shi (JP)

(72) Inventors: Kunio Shiraishi, Otawara (JP); Toshiaki Kawano, Otawara (JP); Hisayasu Yumiza, Otawara (JP); Makoto Takanaka, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 73 days.

(21) Appl. No.: 14/751,549

(22) Filed: Jun. 26, 2015

(65) Prior Publication Data

US 2015/0374323 A1  Dec. 31, 2015

(30) Foreign Application Priority Data

Jun. 26, 2014  (JP) .................................. 2014-131783

(51) Int. Cl.
*G06K 9/00* (2006.01)
*A61B 6/00* (2006.01)

(52) U.S. Cl.
CPC ............ *A61B 6/481* (2013.01); *A61B 6/4441* (2013.01); *A61B 6/463* (2013.01); *A61B 6/487* (2013.01); *A61B 6/504* (2013.01); *A61B 6/542* (2013.01)

(58) Field of Classification Search
None
See application file for complete search history.

(56) References Cited

U.S. PATENT DOCUMENTS

| 8,600,477 B2 * | 12/2013 | Beyar | ...................... A61B 6/12 |
| | | | 128/899 |
| 2007/0276216 A1 * | 11/2007 | Beyar | ...................... A61B 6/12 |
| | | | 600/407 |
| 2010/0329516 A1 * | 12/2010 | Leiblein | ................... G06T 5/50 |
| | | | 382/113 |
| 2012/0114215 A1 * | 5/2012 | Baumgart | ............. G06T 7/0012 |
| | | | 382/132 |

(Continued)

FOREIGN PATENT DOCUMENTS

JP  2005-12771  1/2005
JP  2011-156321  8/2011

*Primary Examiner* — Tahmina Ansari
(74) *Attorney, Agent, or Firm* — Oblon, McClelland, Maier & Neustadt, L.L.P.

(57) ABSTRACT

An X-ray diagnosis apparatus includes an X-ray tube, an X-ray detector, and a processing circuitry. The X-ray tube generates X-rays. The X-ray detector detects the X-rays that have passed through a subject. The processing circuitry calculates, for each of a plurality of X-ray images that are acquired chronologically, an average of pixel values and a reference value based on the pixel values. The processing circuitry extracts, from the plurality of X-ray images, an X-ray image with a relatively large difference between the average and the reference value, an X-ray image with a relatively large ratio between the average and the reference value, or an X-ray image with a relatively large number of pixels each representing a value equal to or larger than the average or the reference value.

26 Claims, 21 Drawing Sheets

(56) References Cited

U.S. PATENT DOCUMENTS

| | | | |
|---|---|---|---|
| 2012/0128226 A1* | 5/2012 | John | A61B 6/481 382/132 |
| 2014/0294152 A1* | 10/2014 | Florent | G06T 7/003 378/62 |
| 2015/0374323 A1* | 12/2015 | Shiraishi | A61B 6/481 378/42 |

* cited by examiner

FIG.6

| Frame # | Area | Ave | Median | Ave-Median |
|---|---|---|---|---|
| 1 | 440649 | 2047 | 2047 | 0 |
| 2 | 440649 | 2044.818 | 2046 | -1.182 |
| 3 | 440649 | 2042.309 | 2043 | -0.691 |
| 4 | 440649 | 2041.396 | 2042 | -0.604 |
| 5 | 440649 | 2041.517 | 2042 | -0.483 |
| 6 | 440649 | 2041.747 | 2042 | -0.253 |
| 7 | 440649 | 2041.422 | 2042 | -0.578 |
| 8 | 440649 | 2041.58 | 2042 | -0.42 |
| 9 | 440649 | 2045.143 | 2042 | 3.143 |
| 10 | 440649 | 2048.333 | 2043 | 5.333 |
| 11 | 440649 | 2051.85 | 2044 | 7.85 |
| 12 | 440649 | 2061.103 | 2047 | 14.103 |
| 13 | 440649 | 2064.531 | 2047 | 17.531 |
| 14 | 440649 | 2064.492 | 2047 | 17.492 |
| 15 | 440649 | 2064.085 | 2046 | 18.085 |
| 16 | 440649 | 2062.303 | 2046 | 16.303 |
| 17 | 440649 | 2059.334 | 2046 | 13.334 |
| 18 | 440649 | 2055.577 | 2045 | 10.577 |
| 19 | 440649 | 2053.239 | 2044 | 9.239 |
| 20 | 440649 | 2051.149 | 2044 | 7.149 |
| 21 | 440649 | 2050.163 | 2043 | 7.163 |
| 22 | 440649 | 2049.597 | 2044 | 5.597 |
| 23 | 440649 | 2048.714 | 2044 | 4.714 |
| 24 | 440649 | 2048.173 | 2044 | 4.173 |
| 25 | 440649 | 2047.019 | 2043 | 4.019 |
| 26 | 440649 | 2046.376 | 2043 | 3.376 |
| 27 | 440649 | 2045.87 | 2043 | 2.87 |
| 28 | 440649 | 2046.276 | 2044 | 2.276 |
| 29 | 440649 | 2046.432 | 2045 | 1.432 |
| 30 | 440649 | 2046.843 | 2045 | 1.843 |
| 31 | 440649 | 2046.557 | 2045 | 1.557 |
| 32 | 440649 | 2046.731 | 2045 | 1.731 |
| 33 | 440649 | 2047.293 | 2046 | 1.293 |

FIG.8A

| Frame # | Area | Ave | Median | Ave-Median | AVERAGE OF THREE FRAMES |
|---|---|---|---|---|---|
| 1 | 440649 | 2047 | 2047 | 0 | -0.591 |
| 2 | 440649 | 2044.818 | 2046 | -1.182 | -0.624333333 |
| 3 | 440649 | 2042.309 | 2043 | -0.691 | -0.825666667 |
| 4 | 440649 | 2041.396 | 2042 | -0.604 | -0.592666667 |
| 5 | 440649 | 2041.517 | 2042 | -0.483 | -0.446666667 |
| 6 | 440649 | 2041.747 | 2042 | -0.253 | -0.438 |
| 7 | 440649 | 2041.422 | 2042 | -0.578 | -0.417 |
| 8 | 440649 | 2041.58 | 2042 | -0.42 | 0.715 |
| 9 | 440649 | 2045.143 | 2042 | 3.143 | 2.685333333 |
| 10 | 440649 | 2048.333 | 2043 | 5.333 | 5.442 |
| 11 | 440649 | 2051.85 | 2044 | 7.85 | 9.095333333 |
| 12 | 440649 | 2061.103 | 2047 | 14.103 | 13.16133333 |
| 13 | 440649 | 2064.531 | 2047 | 17.531 | 16.37533333 |
| 14 | 440649 | 2064.492 | 2047 | 17.492 | 17.70266667 |
| 15 | 440649 | 2064.085 | 2046 | 18.085 | 17.29333333 |
| 16 | 440649 | 2062.303 | 2046 | 16.303 | 15.90733333 |
| 17 | 440649 | 2059.334 | 2046 | 13.334 | 13.40466667 |
| 18 | 440649 | 2055.577 | 2045 | 10.577 | 11.05 |
| 19 | 440649 | 2053.239 | 2044 | 9.239 | 8.988333333 |
| 20 | 440649 | 2051.149 | 2044 | 7.149 | 7.850333333 |
| 21 | 440649 | 2050.163 | 2043 | 7.163 | 6.636333333 |
| 22 | 440649 | 2049.597 | 2044 | 5.597 | 5.824666667 |
| 23 | 440649 | 2048.714 | 2044 | 4.714 | 4.828 |
| 24 | 440649 | 2048.173 | 2044 | 4.173 | 4.302 |
| 25 | 440649 | 2047.019 | 2043 | 4.019 | 3.856 |
| 26 | 440649 | 2046.376 | 2043 | 3.376 | 3.421666667 |
| 27 | 440649 | 2045.87 | 2043 | 2.87 | 2.840666667 |
| 28 | 440649 | 2046.276 | 2044 | 2.276 | 2.192666667 |
| 29 | 440649 | 2046.432 | 2045 | 1.432 | 1.850333333 |
| 30 | 440649 | 2046.843 | 2045 | 1.843 | 1.610666667 |
| 31 | 440649 | 2046.557 | 2045 | 1.557 | 1.710333333 |
| 32 | 440649 | 2046.731 | 2045 | 1.731 | 1.527 |
| 33 | 440649 | 2047.293 | 2046 | 1.293 | 1.512 |

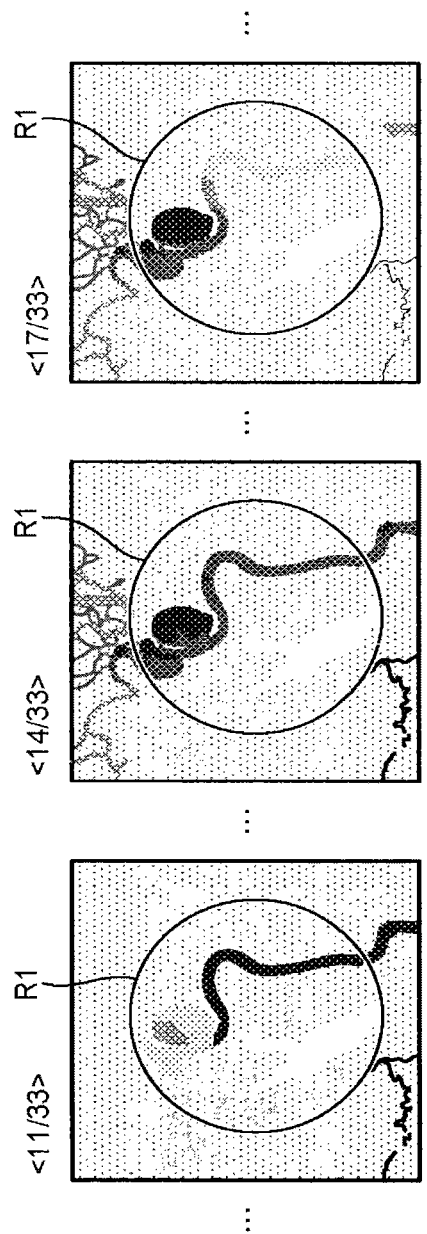

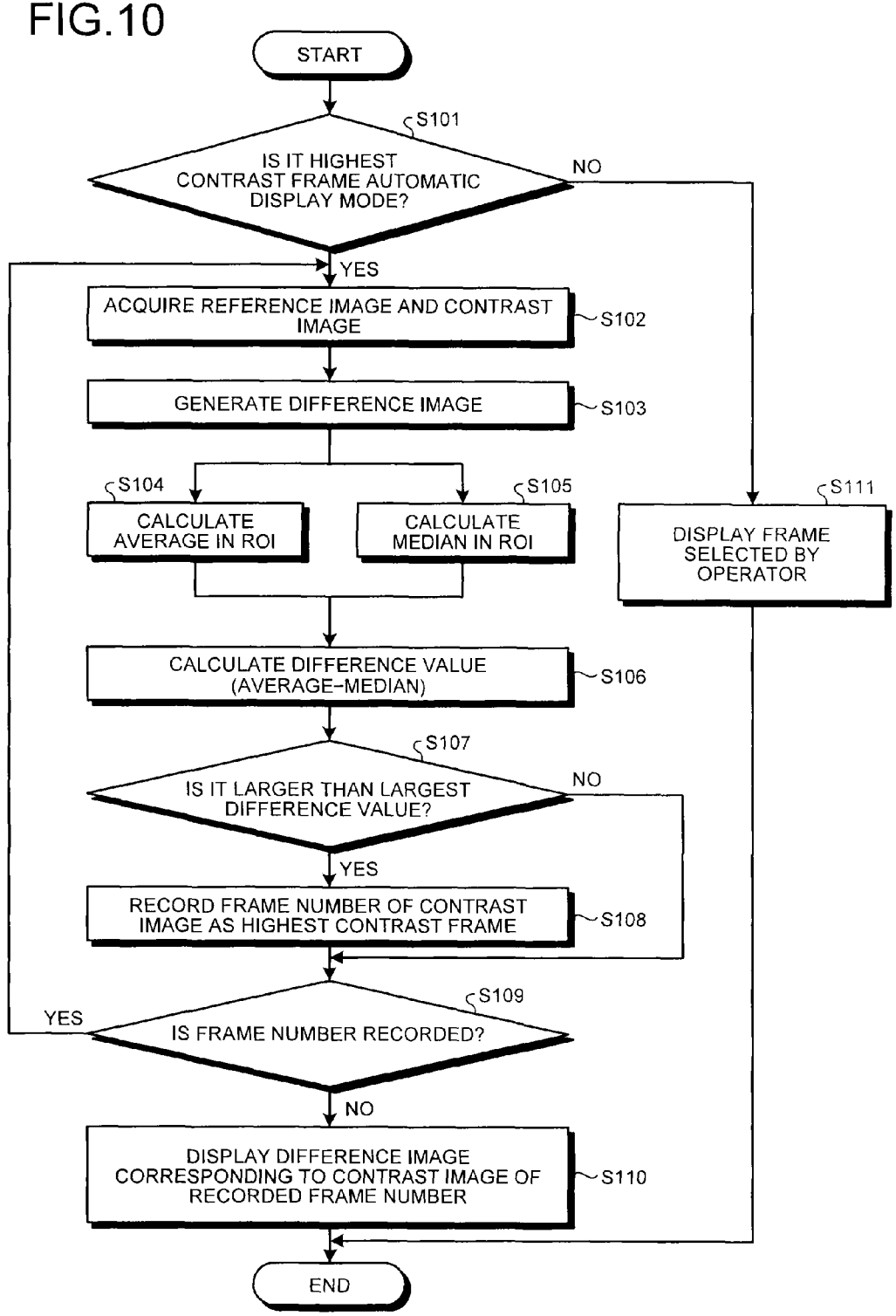

X-RAY DIAGNOSIS APPARATUS INCLUDING PROCESSING CIRCUITRY TO SELECT A ROADMAP IMAGE BASED ON PIXEL VALUES

CROSS-REFERENCE TO RELATED APPLICATIONS

This application is based upon and claims the benefit of priority from Japanese Patent Application No. 2014-131783, filed on Jun. 26, 2014, the entire contents of all of which are incorporated herein by reference.

FIELD

Embodiments described herein relate generally to an X-ray diagnosis apparatus.

BACKGROUND

Conventionally, X-ray images acquired with a contrast material by X-ray diagnosis apparatuses are used for various types of manipulation. For example, X-ray images acquired with a contrast material are used for fluoroscopy roadmap that displays angiograms acquired with a contrast material in order to move a device, such as a catheter or a guide wire used for vascular treatment, forward to a site to be treated. Fluoroscopy roadmap has a fluoroscopy landmark function of acquiring an angiogram depicting the blood stream depending on injection of a contrast material into blood vessels and of displaying the acquired angiogram as superimposed onto a fluoroscopic image and a fluoroscopy subtraction function of canceling the background in order to allow easy observation of the blood vessels and the device.

It is preferable that an image of the blood vessels filled with the contrast material be used for angiograms used for fluoroscopy roadmap in order to allow clear observation of the blood vessels. In general, an operator checks images on a monitor and to use an optimum image. For example, when digital subtraction angiography (DSA) images that are captured in advance after a contrast material is injected into blood vessels are used, the operator selects an image of the blood vessels filled with the contrast material from among DSA image frames. For example, when an angiogram is created from a fluoroscopic image, the operator injects the contrast material during fluoroscopy and, while checking the fluoroscopic image, turns off the fluoroscopy when the blood vessels are filled with the contrast material and uses the last image hold (LID) at that time as an angiogram.

BRIEF DESCRIPTION OF THE DRAWINGS

FIG. 6 is a table showing exemplary selection of a highest contrast frame by a selection unit according to the first embodiment;

FIG. 8A is a table for explaining exemplary averages of difference values obtained by the selection unit according to the first embodiment;

FIG. 9 is a diagram showing an exemplary ROI according to the first embodiment;

FIG. 10 is a flowchart of a processing procedure taken by the X-ray diagnosis apparatus according to the first embodiment;

DETAILED DESCRIPTION

According to an embodiment, an X-ray diagnosis apparatus includes an X-ray tube, an X-ray detector, and a processing circuitry. The X-ray tube generates X-rays. The X-ray detector detects the X-rays that have passed through a subject. The processing circuitry calculates, for each of a plurality of X-ray images that are acquired chronologically, an average of pixel values and a reference value based on the pixel values. The processing circuitry extracts, from the plurality of X-ray images, an X-ray image with a relatively large difference between the average and the reference value, an X-ray image with a relatively large ratio between the average and the reference value, or an X-ray image with a relatively large number of pixels each representing a value equal to or larger than the average or the reference value.

First Embodiment

Figure 1:
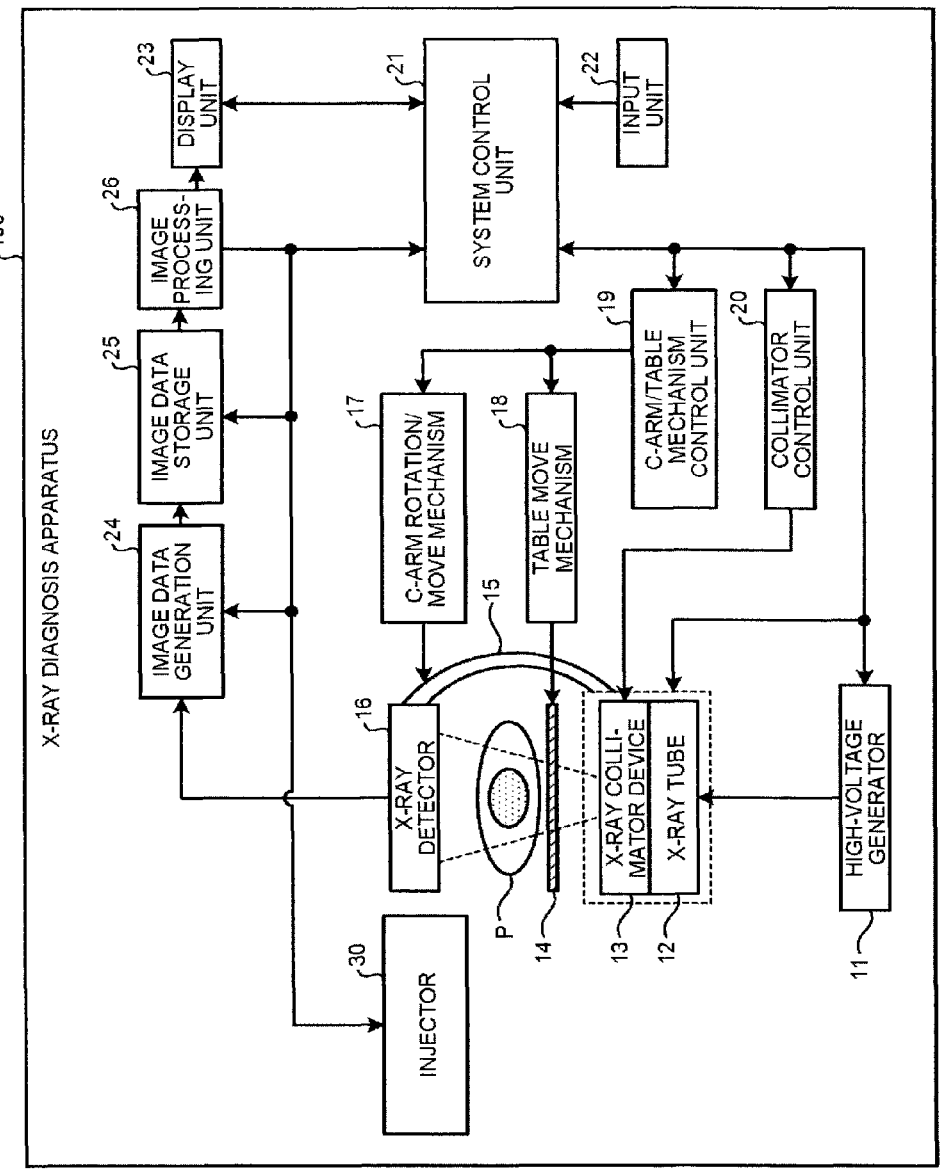
FIG. 1 is a diagram showing an exemplary configuration of an X-ray diagnosis apparatus according to a first embodiment.

FIG. 1 is a diagram showing an exemplary configuration of an X-ray diagnosis apparatus 100 according to a first embodiment. As shown in FIG. 1, the X-ray diagnosis apparatus 100 according to the first embodiment includes a high-voltage generation unit 11, an X-ray tube 12, an X-ray collimator device 13, a table 14, a C-arm 15, and an X-ray detector 16. The X-ray diagnosis apparatus 100 according to the first embodiment further includes a C-arm rotation/move mechanism 17, a table move mechanism 18, a C-arm/table mechanism control unit 19, a collimator control unit 20, a system control unit 21, an input unit 22, and a display unit 23. The X-ray diagnosis apparatus 100 according to the first embodiment further includes an image data generation unit 24, an image data storage unit 25, and an image processing unit 26. The X-ray diagnosis apparatus 100 is connected to an injector 30.

The functions of the above-described respective units are configured as programs and are implemented in a way that circuitry executes the programs. For example, the processing functions respectively implemented by the C-arm/table mechanism control unit 19, the collimator control unit 20, the system control unit 21, the image data generation unit 24, and the image processing unit 26 are stored in a form of computer-executable programs and stored in an image data storage unit 25 (also referred to as an "image data storage circuitry"). The circuitry loads the programs from the image data storage unit 25 and executes the programs, thereby implementing the functions corresponding to the respective programs.

A single circuitry or multiple circuitry may implement the functions. In other words, a single circuitry may load the programs corresponding to the respective functions and implement the corresponding functions, or multiple circuitry may load the programs corresponding to the functions different from one another and implement the corresponding respective functions. The above-described circuitry are processors that implement the functions corresponding to the respective programs in a way that the circuitry loads the programs from the image data storage unit 25 and execute the programs.

The term "processor" used in the above description means, for example, a central preprocess unit (CPU) and a graphics processing unit (GPU), or a circuit such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in a storage circuit. Instead of being stored in a storage circuit, the program may be built directly in a circuit of the processor. In this case, the processor implements a function by loading and executing the program built in the circuit. The processors in the embodiment are not limited to a case in which each of the processors is configured as a single circuit. Multiple separate circuits may be combined to be configured as one processor that implements the respective functions.

The injector 30 is a device for injecting a contrast material from a catheter inserted into a subject P. The contrast material is injected from the injector 30 according to an injection instruction received via the system control unit 21, which will be described below. Specifically, the injector 30 injects the contrast material according to a contrast material injection start instruction, an injection stop instruction, and a contrast material injection conditions including the injection speed that are received from the system control unit 21, which will be described below. The injector 30 can start or stop the injection according to an injection instruction input by an operator directly to the injector 30.

Under the control of the system control unit 21, the high-voltage generation unit 11 generates a high voltage and supplies the generated high voltage to the X-ray tube 12. The X-ray tube 12 generates X-rays using the high voltage supplied from the high-voltage generation unit 11.

Under the control of the system control unit 21, the X-ray collimator device 13 limits the X-ray generated by the X-ray tube 12 so as to selectively expose a region of interest (ROI) of the subject P to the X-rays. For example, the X-ray collimator device 13 includes four slidable collimator blades. By sliding these collimator blades under the control of the collimator control unit 20, the X-ray collimator device 13 limits the X-rays generated by the X-ray tube 12 to expose the subject P to the X-rays. The table 14 is a bed on which the subject P couches and the table 14 is disposed at the top of a couch (not shown). The X-ray diagnosis apparatus 100 does not include the subject P.

The X-ray detector 16 detects the X-rays that have transmitted through the subject P. For example, the X-ray detector 16 includes detection elements that are arrayed in a matrix. Each of the detection elements converts the X-rays that have transmitted through the subject P into electric signals and stores the signals and transmits the stored electric signals to the image data generation unit 24.

The C-arm 15 holds the X-ray tube 12, the X-ray collimator device 13, and the X-ray detector 16. The X-ray tube 12, the X-ray collimator device 13, and the X-ray detector 16 are disposed by the C-arm 15 such that the X-ray tube 12 and the X-ray collimator device 13 are opposed to the X-ray detector 16 with the subject P in between.

The C-arm rotation/move mechanism 17 is a mechanism for rotating and moving the C-arm 15 and the table move mechanism 18 is a mechanism for moving the table 14. By controlling the C-arm rotation/move mechanism 17 and the table move mechanism 18 under the control of the system control unit 21, the C-arm/table mechanism control unit 19 adjusts the rotation and move of the C-arm 15 and the move of the table 14. The C-arm/table mechanism control unit 19 is also referred to as a C-arm/table mechanism control circuitry that loads the program corresponding to the above-described C-arm/table mechanism control function from the image data storage unit 25 and executes the program. By adjusting the aperture of the collimator blades of the X-ray collimator device 13 under the control of the system control unit 21, the collimator control unit 20 controls the area in the subject P to be exposed to X-rays. The collimator control unit 20 is also referred to as a collimator control circuitry that loads the program corresponding to the above-described collimator control function from the image data storage unit 25 and executes the program.

The image data generation unit 24 generates image data, using the electric signals converted from the X-rays by the X-ray detector 16 and stores the generated image data in the image data storage unit 25. For example, the image data generation unit 24 performs current-voltage conversion, analog-digital (A/D) conversion, and parallel-serial conversion on the electric signals received from the X-ray detector 16 to generate image data. The image data generation unit 24 generates multiple X-ray images of the subject P injected with the contrast material that are captured sequentially. The image data generation unit 24 stores the generated X-ray images in the image data storage unit 25. The image data generation unit 24 is also referred to as an image data generation circuitry that loads the program corresponding to the above-described image data generation function from the image data storage unit 25 and executes the program.

The image data storage unit 25 stores the image data generated by the image data generation unit 24. For example, the image data storage unit 25 stores the data of images of the subject P to which the contrast material is administered that are captured chronologically. The image data storage unit 25 is also referred to as an image data storage circuitry that stores the programs corresponding to the respective functions.

The image processing unit 26 performs various types of image processing on the image data stored in the image data storage unit 25. For example, by processing multiple X-ray images captured chronologically and stored in the image data storage unit 25, the image processing unit 26 generates video images. The image processing unit 26 is also referred to as an image processing circuitry that loads the program corresponding to the above-described image processing function from the image data storage unit 25 and executes the program.

The input unit 22 receives various instructions from the operator, such as a doctor or a technologist, who operates the X-ray diagnosis apparatus 100. For example, the input unit 22 includes a mouse, a keyboard, a button, a trackball, a joystick, etc. The input unit 22 transfers an instruction received from the operator to the system control unit 21. For example, the input unit 22 receives a designation instruction for designating an arbitrary area in an X-ray image. The input unit 22 is also referred to as an input circuitry.

The display unit 23 displays a graphical user interface (GUI) for receiving instructions from the operator and image data stored in the image data storage unit 25, etc. For example, the display unit 23 includes a monitor. The display unit 23 may include multiple monitors. The display unit 23 is also referred to as a display.

The system control unit 21 controls whole operations of the X-ray diagnosis apparatus 100. For example, the system control unit 21 controls the high-voltage generation unit 11 according to an instruction from the operator that is transferred from the input unit 22 to adjust the voltage to be supplied to the X-ray tube 12, thereby controlling the amount of X-rays to which the subject P is exposed and on/off of exposure. For example, the system control unit 21 further controls the C-arm/table mechanism control unit 19 according to an instruction from the operator to adjust the move of the table 14. For example, the system control unit 21 further controls the collimator control unit 20 according to an instruction from the operator to adjust the aperture of the collimator blades of the X-ray collimator device 13, thereby controlling the exposed area at which the subject P is exposed to X-rays.

In accordance with an instruction from the operator, the system control unit 21 controls the image data generation processing performed by the image data generation unit 24, the image processing performed by the image processing unit 26, or analysis processing. The system control unit 21 performs control to display, for example, the GUI for receiving instructions from the operator or images stored in the image data storage unit 25 on the monitor of the display unit 23. The system control unit 21 transmits a contrast material injection start signal and a contrast material injection end signal to the injector 30 to control the contrast material injection timing. The system control unit 21 is also referred to as a system control circuitry that loads the program corresponding to the above-described system control function from the image data storage unit 25 and executes the program.

The exemplary configuration of the X-ray diagnosis apparatus 100 has been described. The X-ray diagnosis apparatus 100 according to the embodiment configured as described above makes it possible to increase the efficiency of manipulation depending on the control by the system control unit 21 to be described in detail below. Specifically, the X-ray diagnosis apparatus 100 automatically selects a certain X-ray image from among multiple images acquired chronologically, which increases the efficiency of manipulation. For example, the X-ray diagnosis apparatus 100 accurately selects an X-ray image captured when the blood vessels are most filled with the contrast material from among the multiple X-ray images acquired chronologically with the contrast material, which increases the efficiency of manipulation.

As described above, X-ray images acquired with a contrast material by X-ray diagnosis apparatuses are used for various types of manipulation. For example, for fluoroscopy roadmap, angiograms of blood vessels filled with a contrast material are used. In conventional technologies, because an operator selects an angiogram of blood vessels filled with a contrast material while checking images on a monitor, the efficiency of manipulation may lower. For example, when an angiogram is selected from multiple DSA images, it may take time for the operator to check the images. When an LIH image is used, the operator may have to get used to take the timing at which fluoroscopy is turned off at, for example, a site where the blood flows fast or may have to increase the amount of the contrast material.

As descried above, according to conventional technologies, an operator manually selects an X-ray image captured when blood vessels are most filled with a contrast material. Furthermore, a technology for automatically detecting a contrast material contained in an X-ray image is also known in recent years. The technology allows detection of flowing of the contrast material into blood vessels by using the characteristics in that a shade appears in the X-ray image due to the contrast material entering the blood vessels and accordingly the area corresponding to the blood vessels gets dark so that the average of the pixel values decreases, and allows detection of flowing of the contrast material into the blood vessels by using the characteristics in that dispersion of the pixel values (statistics, such as distribution and standard deviation) increases.

With the above-described technology where the contrast material is automatically detected, however, an X-ray image captured when the blood vessels are most filed with the contrast material is not necessarily selected depending on the X-ray output stability, the after-image characteristics of the detector, and the body motion of the subject. For example, when an X-ray image captured when the blood vessels are most filed with the contrast material is selected from multiple DSA images and if the X-ray output varies or if an after-image of the detector or a body motion of the subject occurs when an image to be subtracted is captured, the pixel values vary also in the background area. As a result, even when an X-ray image with the largest (smallest) average of the pixel values or an X-ray image with the largest dispersion of the pixel values is selected, the X-ray image is not necessarily an X-ray image captured when the blood vessels are most filed with the contrast material.

Figure 2:
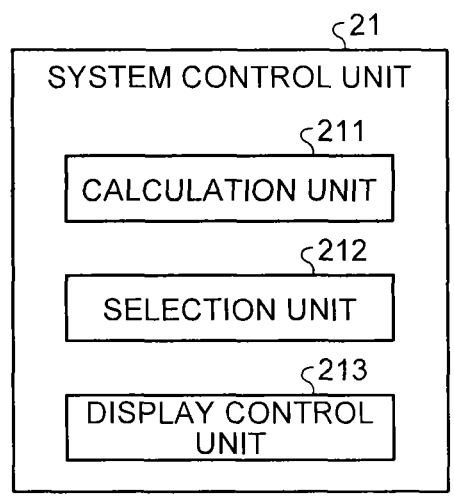
FIG. 2 is a diagram showing an exemplary configuration of a system control unit according to the first embodiment.

The X-ray diagnosis apparatus 100 according to the first embodiment increases the efficiency of manipulation by accurately selecting an X-ray image captured when the blood vessels are most filed with the contrast material from among multiple X-ray images that are acquired with the contrast material chronologically. FIG. 2 is a diagram showing an exemplary configuration of the system control unit 21 according to the first embodiment. As shown in FIG. 2, the system control unit 21 according to the first embodiment includes a calculation unit 211, a selection unit 212, and a display control unit 213. In other words, the system control circuitry that implements the system control function performs the processing, which will be described below, by loading the programs corresponding to the functions of the calculation unit 211, the selection unit 212, and the display control unit 213 from the image data storage unit 25 and executing the programs.

Figure 3:
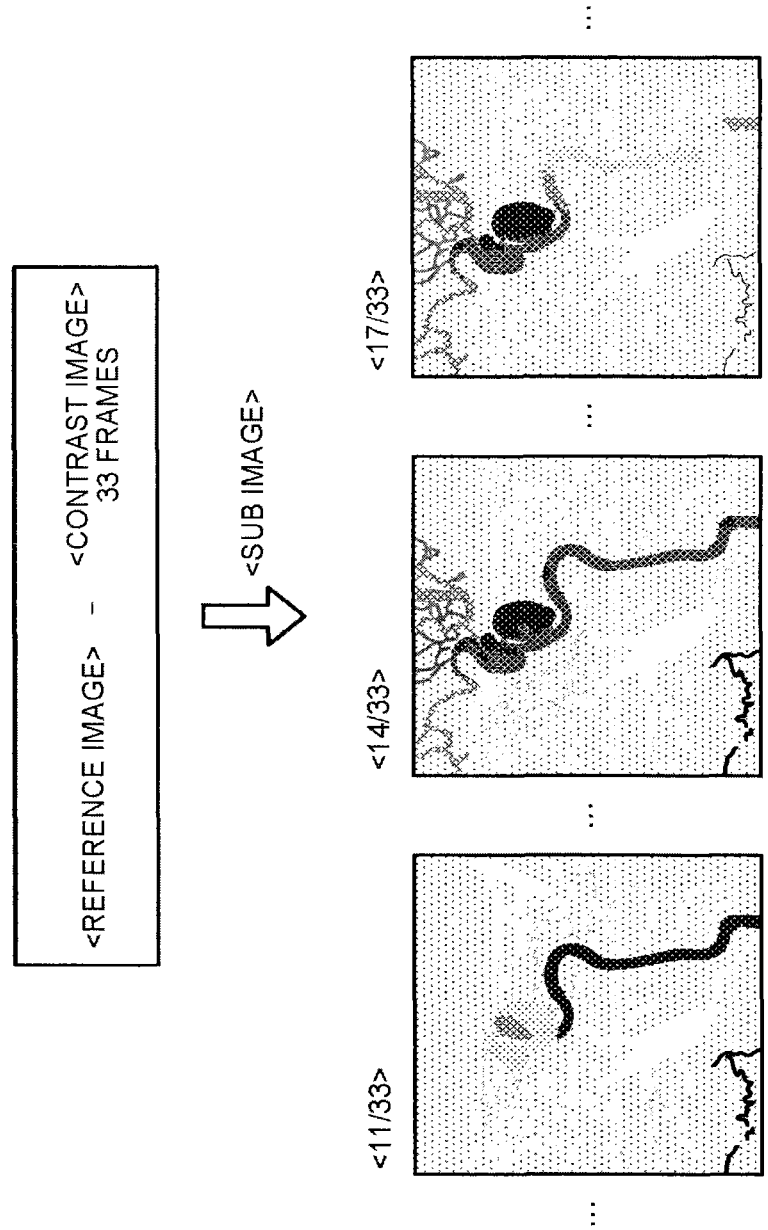
FIG. 3 is a diagram illustrating exemplary X-ray images to be processed by a calculation unit according to the first embodiment.

The calculation unit 211 calculates an average of pixel values and a reference value based on the pixel values for each of the multiple X-ray images acquired chronologically. Specifically, the calculation unit 211 calculates an average of pixel values and a median or a mode of the pixel values that serves as a reference value based on the pixel values. The calculation unit 211 according to the first embodiment calculates the average of the pixel values and at least any one of the median of the pixel values and the mode of the pixel values for each of the multiple X-ray images acquired chronologically. Specifically, the calculation unit 211 calculates the average and at least any one of the median and the mode for each of the multiple difference images each obtained by subtracting the back ground from each of the multiple X-ray images acquired with the contrast material chronologically. FIG. 3 is a diagram illustrating exemplary X-ray images to be processed by the calculation unit 211 according to the first embodiment.

For example, as shown in FIG. 3, the calculation unit 211 processes subtraction (SUB) images each obtained by subtracting each of contrast images (33 frames) that are images sequentially captured after the contrast material is injected from a reference image that is an image before injection of the contrast material at the time when image capturing with the contrast material starts. In other words, for all of the SUB images of 33 frames (1/33 to 33/33), the calculation unit 211 calculates an average of the pixel values and at least one of a median of the pixel values, and a mode of the pixel values. The average of the pixel values represents the value obtained by dividing the total of the pixel values of the pixels to be processed by the number of pixels. The median of the pixel values represents the center value of the pixels to be processed. The mode of the pixel values represents the value that appears most often among the pixel values of the pixels to be processed.

Depending on based on which value an X-ray image is selected, which of an average, a median, and a mode is calculated is changed arbitrarily. The pixels to be processed are the pixels contained in a region of interest (ROI) that is set in the SUB images. The ROI may be set at any area in the SUB images, or the whole image may be set for an ROI. The first embodiment will be descried by using an exemplary case where the whole image is set for an ROI. The example shown in FIG. 3 is an example only and does not limit embodiments. For example, the contrast images are not limited to 33 frames, and they may be less than 33 frames or larger than 33 frames. Furthermore, an SUB image may be obtained not only by "subtracting a contrast image from a reference image" but also by "subtracting a reference image from a contrast image".

The following descriptions refer back to FIG. 2. The selection unit 212 selects a certain X-ray image from the multiple X-ray images according to the difference between the average and the median or the node, the ratio between the average and the median or the node, or the number of pixels each representing a value equal to or larger than the average, the median, or the node. Specifically, the selection unit 212 selects, from among the multiple X-ray images, an X-ray image with a relatively large difference between the average and the median or the node, an X-ray image with a relatively large ratio between the average and the median or the node, or an X-ray image with a relatively large number of pixels each representing a value equal to or larger than the average, the median, or the node. In other words, the selection unit 212 selects, from among multiple X-ray images, an X-ray image with a relatively large difference between the average and the reference value, an X-ray image with a relatively large ratio between the average and the reference value, or an X-ray image with a relatively large number of pixels each representing a value equal to or larger than the average or the reference value. The selection unit 212 is also referred to as an extraction unit that extracts an X-ray image as described above.

More specifically, the selection unit 212 selects, as a contrast image in which the contrast obtained with the contrast material is proper, an X-ray image with a relatively large difference between the average and the reference value, an X-ray image with a relatively large ratio between the average and the reference value, or an X-ray image with a relatively large number of pixels each representing a value equal to or larger than the average or the reference value. For example, the selection unit 212 selects, as a highest contrast image with the highest contrast obtained with the contrast material, an X-ray image with the largest difference between the average and the median or the node, an X-ray image with the highest ratio between the average and the median or the node, or an X-ray image with the largest number of pixels each representing the average, the median, or the node. For the first embodiment, an exemplary case where an X-ray image with the largest difference between the average and the median is selected as a highest contrast image will be described below. The highest contrast image will be referred to as a highest contrast frame below as necessary.

Figure 4:
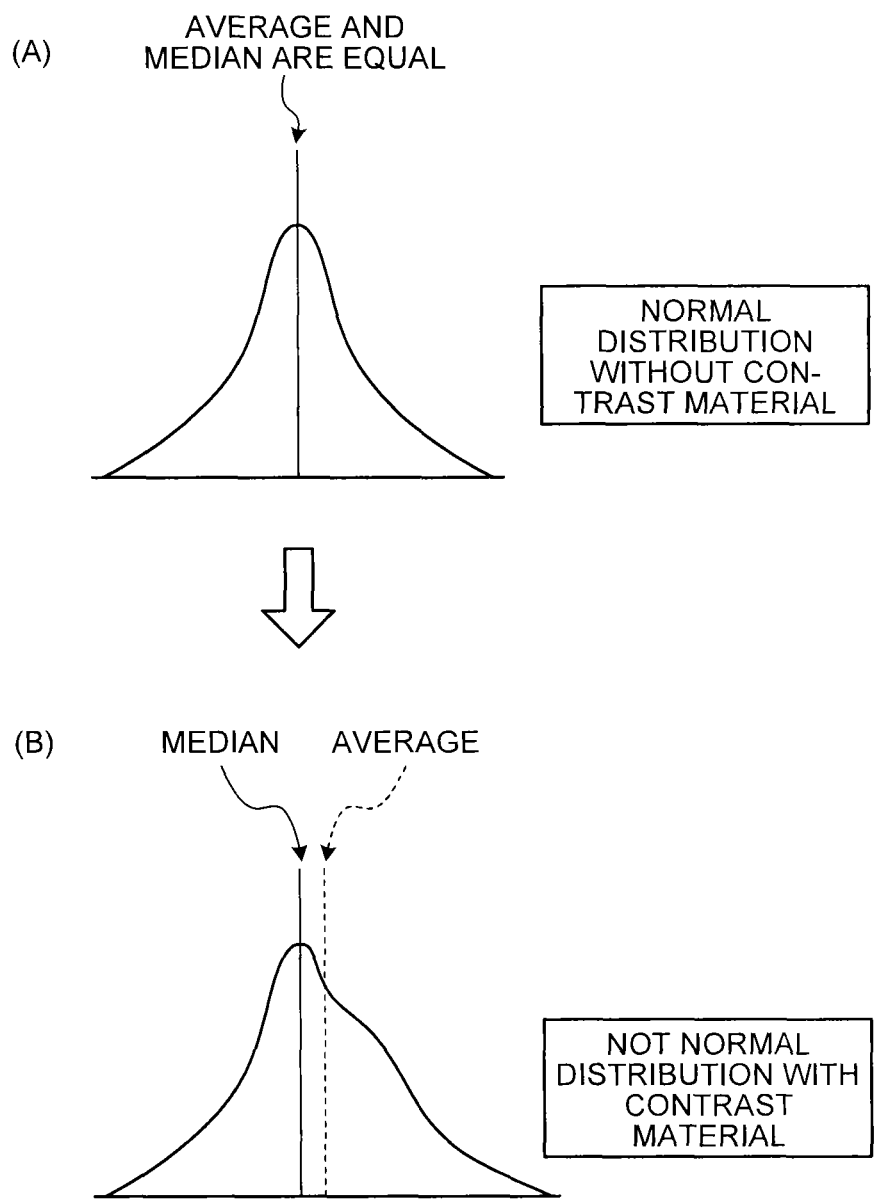
FIG. 4 is a diagram for explaining the pixel values of a SUB image according to the first embodiment.
Figure 5:
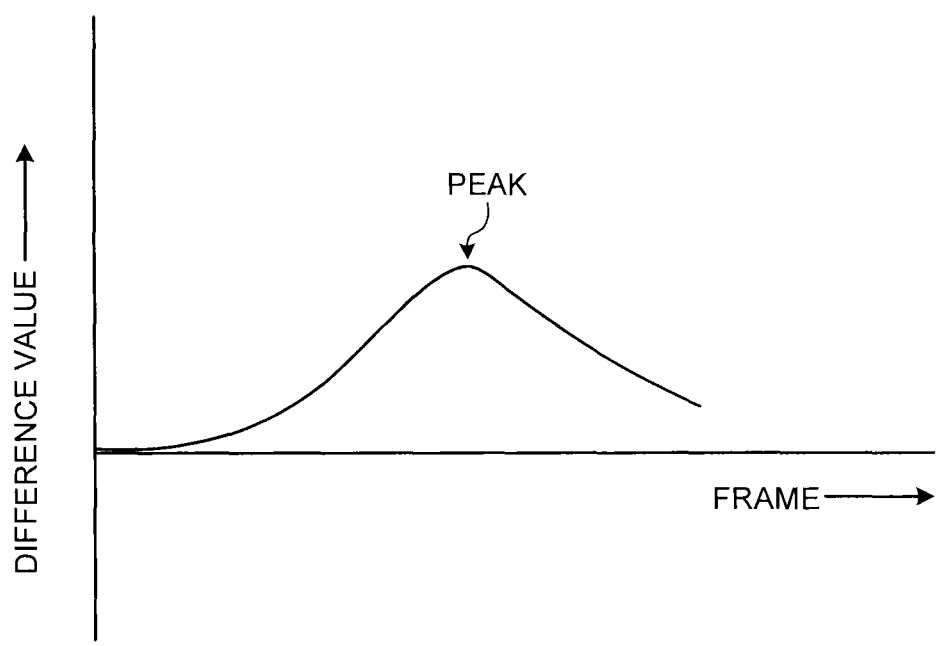
FIG. 5 is a diagram for explaining the pixel values of SUB images according to the first embodiment.

For example, the selection unit 212 calculates, for each SUB image, a difference value between the average of pixel values and the median of the pixel values calculated by the calculation unit 211 and selects an SUB image representing the largest difference value among the calculated difference values as a highest contrast image. With reference to FIGS. 4 and 5, the average and the median of the pixel values of a SUB image will be described. FIGS. 4 and 5 are diagrams each for explaining the pixel values of a SUB image according to the first embodiment. FIG. 4 shows a histogram of the pixel values of the SUB image. FIG. 5 shows a change in the difference value between the average and the median of the pixel values of the SUB images from the multiple X-ray images acquired with the contrast material chronologically.

Because a SUB image is obtained by "subtracting a contrast image from the reference image" as described above, the pixels corresponding to the blood vessels into which the contrast material flows in the SUB image are obtained by "subtracting bright pixels from dark pixels". On the other hand, the pixels of the surroundings (background) into which the contrast material does not flow are obtained by "subtracting bright pixels from bright pixels". Accordingly, the pixels corresponding to the blood vessels into which the contrast material flows in the SUB image have higher pixel values than those of the pixels of the background. In other words, the number of pixels having higher pixel values gradually increases as the contrast material flows into, and the number of pixels having higher pixel values gradually decreases as the contrast material flows out.

It is assumed that the difference value of the pixels of the background is "0" if there is no change between the reference image and the contrast image; however, practically, it rarely happens that the difference values of all the pixels of the background are "0" because, as described above, there a change occurs depending on the X-ray output stability, the after-image characteristics of the detector, and the body motion of the subject. In other words, as shown in FIG. 4(A), the histogram of the difference values in the SUB image without the contrast material represents a normal distribution where the average and the median of the pixel values are the same.

Because the pixel values increase when the contrast material flows into as described above, as shown in FIG. 4(B), the average of the pixel values increases and accordingly the normal distribution is not shown. If the ROI that is set is an area sufficiently larger than the area of the blood-vessels, the pixel values of the background occupying most of the pixels in the ROI correspond to the median. In other words, an increase in the area into which the contrast material flows gradually increases the number of pixels with high pixel values and accordingly increases the difference between the average and the median. Thus, as shown in FIG. 5, the selection unit 212 calculates a difference value of each of the frames of the SUB images and selects a frame with the peak difference value as a highest contrast frame.

Figure 7:
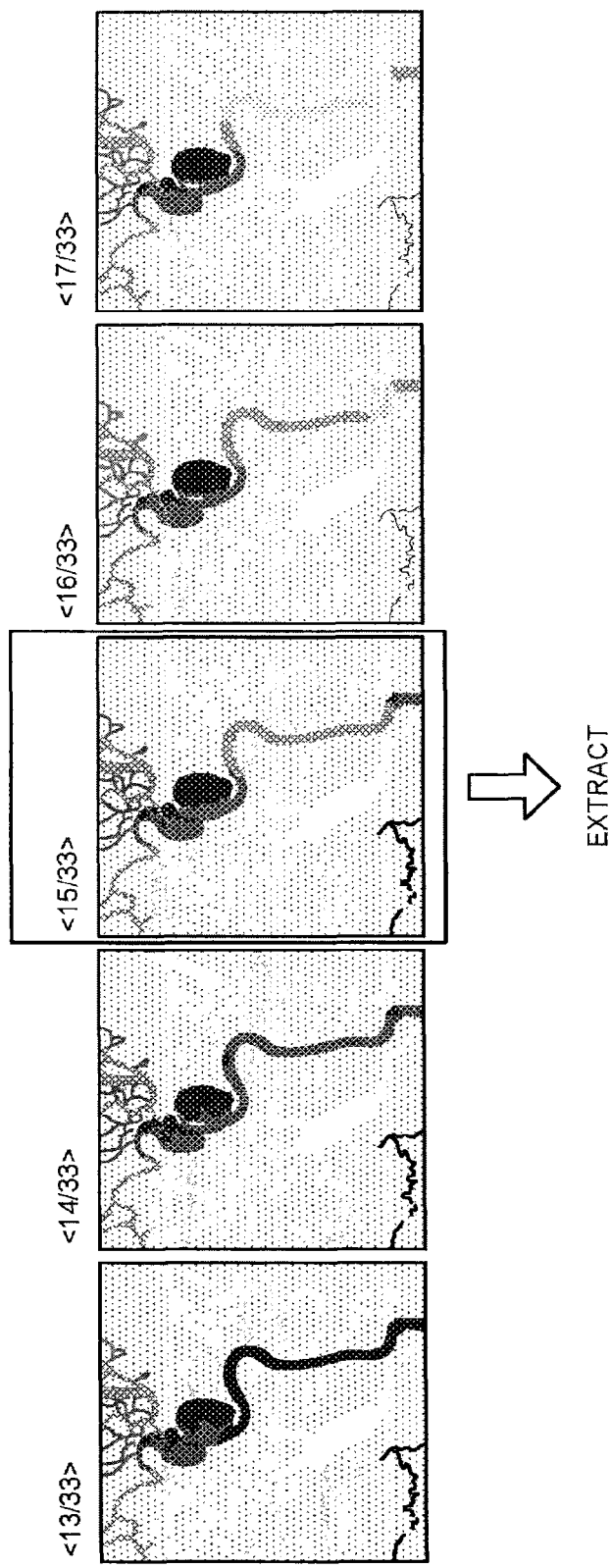
FIG. 7 is a diagram showing exemplary selection of a highest contrast frame by a selection unit according to the first embodiment.

Exemplary selecting of a highest contrast frame will be described with reference to FIGS. 6 and 7. FIGS. 6 and 7 are a table and a diagram both showing exemplary selecting of a maximum contrast frame by the selection unit 212 according to the first embodiment. FIG. 6 shows exemplary averages, medians, and difference values of SUB image of 33 frames. FIG. 7 shows an exemplary selected SUB image.

For example, as shown in FIG. 6, when the calculation unit 211 calculates an average (Ave) and a median (Median) of the pixel values of the number of pixels (Area) "440649" contained in the ROI for the SUB images of the frames (Frame) "1 to 33", the selection unit 212 calculates a difference value (Ave−Median) between the average and the median and selects Frame 15 representing the largest value from among the calculated difference values as a highest contrast frame. As shown in FIG. 7, the image is an image of the blood vessels in the ROI that are filled with the contrast material from among the X-ray images acquired chronologically. In other words, according to the above-described processing, the selection unit 212 can select and extract an X-ray image acquired when the blood vessels are most filled with the contrast material.

For the above-described example, the case has been descried where the difference between the average and the median of the pixel values is used; however, embodiments are not limited to this, and a mode may be used instead of the median. In such a case, the mode corresponds to the pixel values of the background and the processing can be performed in the same manner as the above-described processing.

Figure 8B:
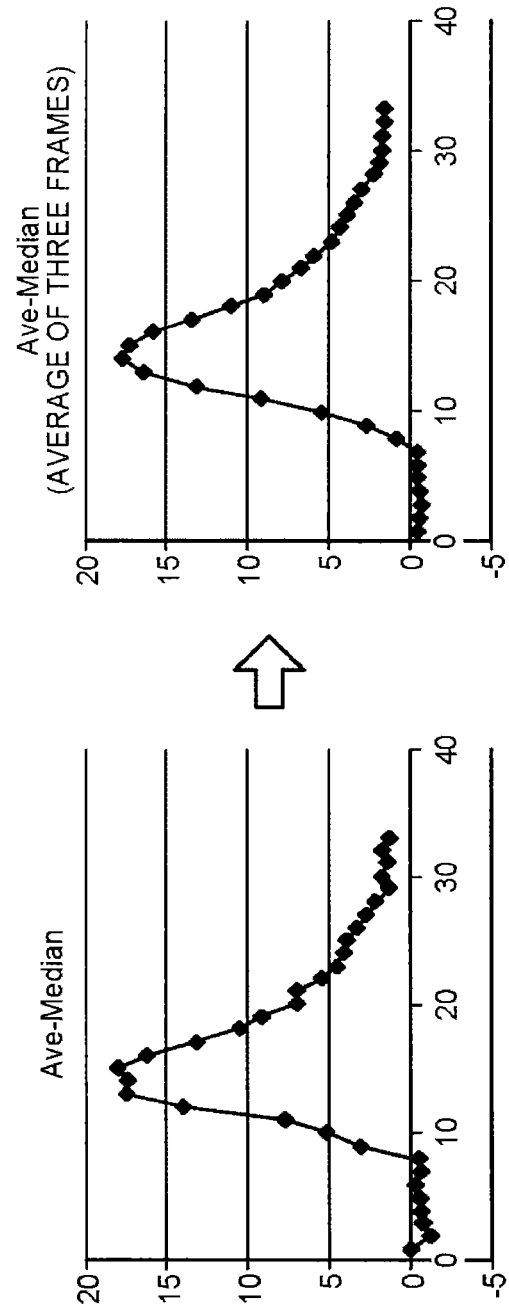
FIG. 8B is a diagram for explaining exemplary averages of difference values obtained by the selection unit according to the first embodiment.

For the above-described example, the case has been descried where the difference value of the SUB image is calculated separately per frame; however, embodiments are not limited to this. For example, the difference values of multiple frames may be averaged. In such a case, for example, the selection unit 212 uses the average between frames successive chronologically as a difference value of each frame. FIGS. 8A and 8B are diagrams for explaining an exemplary average of difference values obtained by the selection unit 212 according to the first embodiment. FIG. 8A shows exemplary averages of difference values of the SUB images of 33 frames. FIG. 8B shows a graph in which the horizontal axis represents the frame number and the vertical axis represents the difference value, showing exemplary changes in the difference values obtained by the averaging.

For example, when calculating a difference value of each frame, the selection unit 212 calculates a value obtained by averaging difference values of three frames of a frame, a frame just forward the frame, and a frame just behind the frame acquired chronologically as a difference value of each of frame. For example, as shown in FIG. 8A, the selection unit 212 calculates "the average of three frames: −0.624333333" obtained by averaging a difference value (Ave−Median) "0" of Frame 1, a difference value (Ave−Median) "−1.182" of Frame 2, and a difference value (Ave−Median) "−0.691" of Frame 3. In the same manner, the selection unit 212 calculates, as the difference value of each frame, a value obtained by averaging the differences of the three frames acquired chronologically, i.e., a frame and the forward and behind frames with respect to the frame.

Because there is no frame forward Frame 1, the selection unit 212 calculates a value obtained by averaging the difference values of two frames, i.e., Frame 1 and Frame 2, as the difference value of Frame 1. Similarly, because there is no frame behind Frame 33, the selection unit 212 calculates a value obtained by averaging the difference values of two frames, i.e., Frame 32 and Frame 33, as the difference value of Frame 33. The example shown in FIG. 8A is an example only, and embodiments are not limited to this. For example, the number of frames to be averaged is not limited to three, and an arbitrary number of frames may be averaged.

As described above, because the difference values of the frames successive over time are averaged to obtain a difference value of each frame, for example, as shown in FIG. 8B, the transition of the difference values obtained by averaging (the graph shown on the right in FIG. 8B) is much smoother than the transition of the difference values only according to each frame (the graph shown on the left in FIG. 8B). For example, while the difference value lowers at the peak in the case of the difference values only according to each frame, there is not such a part in the case of the difference values obtained by averaging. In other words, averaging the difference values of frames reduces the noise effects and leads to values accurately reflecting the changes in the shade obtained with the contrast material. This makes it possible to select a more accurate highest contrast frame.

For the above-described embodiment, the case where the whole image is set for the ROI; however, embodiments are not limited to this, and any ROI may be set on the image. FIG. 9 is a diagram showing an exemplary ROI according to the first embodiment. For example, as shown in FIG. 9, an ROI "R1" is set in the SUB images, the average, the median, and the mode of the pixel values contained in the set RI are calculated per frame, and a highest contrast frame is selected according to the difference values. The ROI may be set by the operator via the input unit 22 on the SUB images. Alternatively, the ROI may be automatically set such that it covers pixels whose pixel values change significantly in the SUB images. The ROI setting may be accepted at an arbitrary time and controlled such that a highest contrast frame is selected each time an ROI is set.

The following descriptions refer back to FIG. 2. The display control unit 213 performs control to cause the display unit 23 to display the highest contrast frame selected by the selection unit. For example, the display control unit 213 causes the display unit 23 to display a SUB image corresponding to the selected frame number as the highest contrast frame that is selected by the selection unit 212.

With reference to FIG. 10, the processing performed by the X-ray diagnosis apparatus 100 according to the first embodiment will be described here. FIG. 10 is a flowchart of a processing procedure taken by the X-ray diagnosis apparatus 100 according to the first embodiment. FIG. 10 shows the processing to be performed after a contrast material is injected and X-ray images are captured chronologically. FIG. 10 shows a case where the difference values of frames are not averaged and are calculated separately.

As shown in FIG. 10, in the X-ray diagnosis apparatus 100 according to the first embodiment, when it is a highest contrast frame automatic display mode (YES at step S101), the image processing unit 26 acquires a reference image and a contrast image from the image data storage unit 25 (step S102) and generates a difference image (step S103). When the difference image is generated, the calculation unit 211 calculates an average of the pixel values of the pixels in an ROI (step S104) and calculates a median of the pixel values of the pixels in the ROI (step S105).

Using the average and the median calculated by the calculation unit 211, the selection unit 212 calculates a difference value (average−median) according to the order of the frames (step S106) and determines whether the calculated difference value is larger than the current largest difference value (step S107). When the selection unit 212 determines that the calculated difference value is larger than the current largest difference value (YES at step S107), the selection unit 212 records, as a highest contrast frame, the frame number of the contrast image of the frame (SUB image) for which the difference value is calculated (step S108).

On the other hand, when the selection unit 212 determines that the calculated difference value is not larger than the current largest difference value (NO at step S107), the selection unit 212 does not record the frame number and goes to determination at step S109. After recording the frame number because the calculated difference value is larger than the current largest difference value (YES at step S107), or after determining that the calculated difference value is not larger than the current largest difference value, the selection unit 212 determines whether the frame number is recorded (NO at step S109). As described above, when the difference values are viewed according to the order of the frames, the difference value increases to the peak and thereafter decreases (see, for example, FIG. 5). The selection unit 212 thus searches for the largest difference value by comparing the difference values according to the order of the frames and records the frame number representing the largest difference value. When the frame number is not recorded, the selection unit 212 determines that the difference value starts decreasing and selects the frame of the currently-recorded frame number as a highest contrast frame.

For the determination on whether the frame number is recorded, the fact that the frame number is not recorded even once may be used as a condition. Alternatively, in consideration of fluctuation due to noise, the fact that the frame number is not recorded for multiple times sequentially may be used as a condition. For example, the selection unit 212 determines that the frame number is not recorded when the frame number is not recorded twice sequentially. When, at step S109, the selection unit 212 determines that the frame number is recorded (YES at step S109), the X-ray diagnosis apparatus 100 returns to step S102 and continues the processing.

On the other hand, when the selection unit 212 determines that the frame number is not recorded (NO at step S109), the display control unit 213 causes the display unit 23 to display the difference image (SUB image) corresponding to the contrast image of the recorded frame number (step S110). When, at step S101, it is not the highest contrast frame automatic display mode (NO at step S101), the display control unit 213 causes the display unit 23 to display an SUB image of a frame selected by the operator (step S111).

For the above-described processing procedure, the case where the difference values are compared according to the order of the frames to select a highest contrast frame has been described; however, embodiments are not limited to this. For example, the difference values may be calculated for all frames and the frame number representing the largest value from among all of the calculated difference values may be recorded.

As described above, according to the first embodiment, the calculation unit 211, calculates an average of pixel values and at least any one of a median of the pixel values, and a mode of the pixel values for each of multiple X-ray images acquired chronologically. According to the difference between the average and the median or the mode, the selection unit 212 selects a certain X-ray image from among the multiple X-ray images. Accordingly, the X-ray diagnosis apparatus 100 according to the first embodiment can accurately select an X-ray image with a difference between the average and the median of the pixel values or the average and the mode of the pixel values from among the multiple X-ray images, which makes it possible to increase the efficiency of manipulation.

Furthermore, according to the first embodiment, the calculation unit 211 calculates at least any one of the average, the median, and the mode for each of the multiple difference images each obtained by subtracting the background from each of the multiple X-ray images that are acquired with the contrast material chronologically. The selection unit 212 selects an X-ray image with the largest difference between the average and the median or the mode as a highest contrast image with the highest contrast obtained with the contrast material. Accordingly, the X-ray diagnosis apparatus 100 according to the first embodiment can accurately select an X-ray image captured when the blood vessels are most filled with the contrast material, which makes it possible to increase the efficiency of manipulation.

Second Embodiment

For the above-described embodiment, the case where the highest contrast frame is selected from the captured multiple X-ray images has been described. For a second embodiment, a case where a highest contrast frame is selected in real time during image capturing will be described. The X-ray diagnosis apparatus 100 according to the second embodiment is different from the X-ray diagnosis apparatus 100 according to the first embodiment only in the processing timing. The difference will be described below with reference to FIG. 11.

Figure 11:
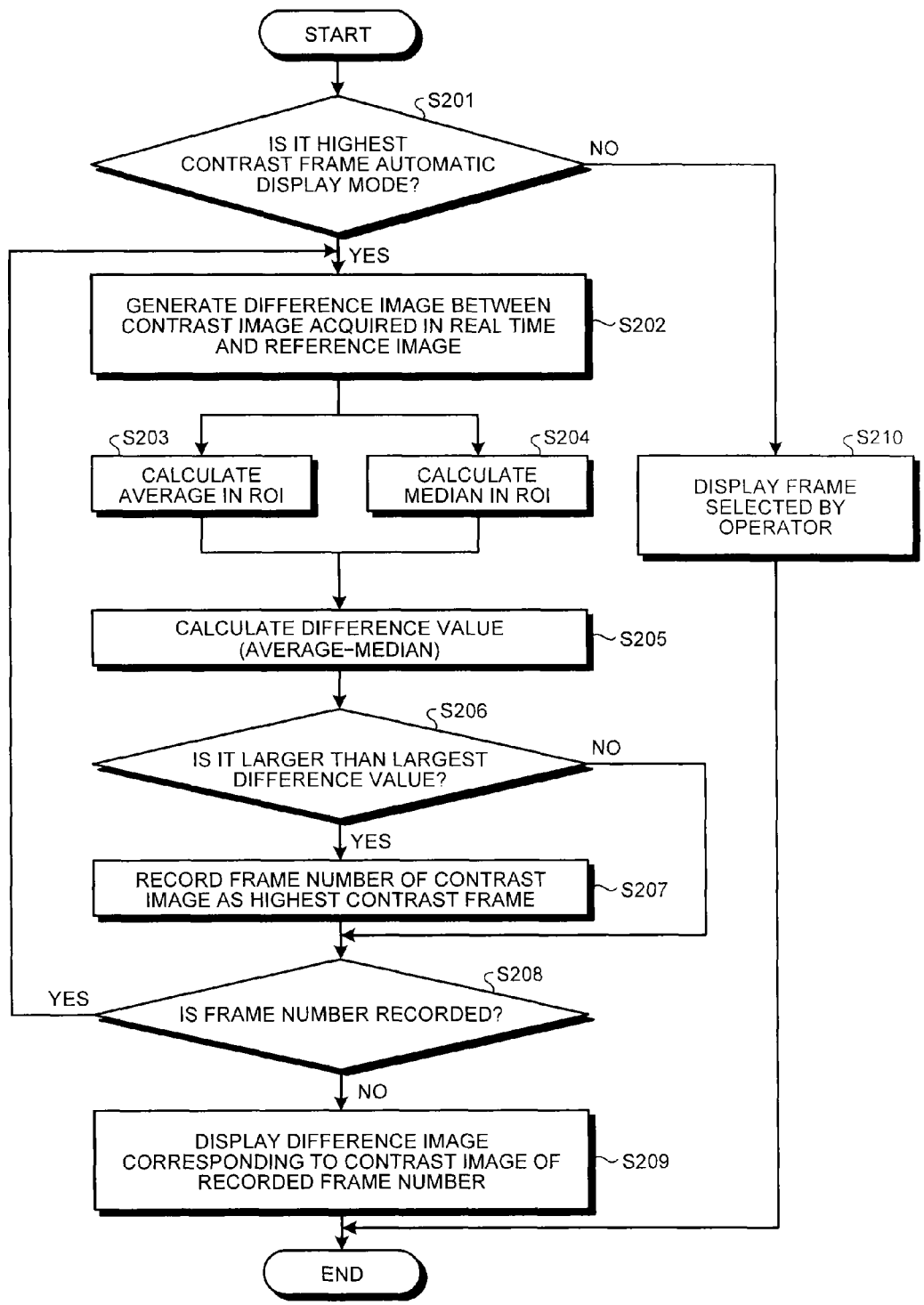
FIG. 11 is a flowchart of a processing procedure taken by the X-ray diagnosis apparatus according to a second embodiment.

FIG. 11 is a flowchart of a processing procedure taken by the X-ray diagnosis apparatus 100 according to the second embodiment. FIG. 11 shows a case where an average and a median of pixel values of pixels in a ROI are calculated. FIG. 11 shows a case where difference values of respective frames are not averaged and are calculated separately.

As shown in FIG. 11, in the X-ray diagnosis apparatus 100 according to the second embodiment, when it is a highest contrast frame automatic display mode (YES at step S201), the image processing unit 26 generates a difference value between a contrast image acquired in real time and a reference image (step S202). When the difference image is generated, the calculation unit 211 calculates an average of pixel values of pixels in an ROI (step S203) and calculates a median of the pixel values of the pixels in the ROI (step S204).

Using the average and the median, the selection unit 212 then calculates a difference value (median−average) (step S205) and determines whether the calculated difference value is larger than the current largest difference value (step S206). When the selection unit 212 determines that the calculated difference value is larger than the current largest difference value (YES at step S206), the selection unit 212 records, as a highest contrast frame, the frame number of the contrast image of the frame (SUB image) for which the difference value is calculated (step S207).

On the other hand, when the selection unit 212 determines that the calculated difference value is not larger than the current largest difference value (NO at step S206), the selection unit 212 does not record the frame number and goes to determination at step S208. The determination at step S208 is executed in the same manner as that according to the first embodiment. At step 3208, when the selection unit 212 determines that the frame number is recorded (YES at step S208), the X-ray diagnosis apparatus 100 returns to step S202 and continues the realtime processing.

On the other hand, when the selection unit 212 determines that the selection unit 212 does not record the frame number (NO at step S208), the display control unit 213 causes the display unit 23 to display the difference image (SUB image) corresponding to the contrast image of the recorded frame number (step S209). When it is not the highest contrast frame automatic display mode at step S201 (NO at step S201), the display control unit 213 causes the display unit 23 to display an SUB image of a frame selected by the operator (step S210).

As described above, the X-ray diagnosis apparatus 100 according to the second embodiment can select a highest contrast frame in real time while acquiring X-ray images with the contrast material, which makes it possible to increase the efficiency of manipulation.

Third Embodiment

For the above-described embodiment, the case where the highest contrast frame is selected from the multiple X-ray images has been described. For a third embodiment, a case where a highest contrast frame is selected as an angiogram (hereinafter, referred to as a mask image) for a fluoroscopy roadmap will be described. The X-ray diagnosis apparatus 100 according to the third embodiment is different from the X-ray diagnosis apparatus 100 according to the first embodiment in the processing performed by the selection unit 212. The difference will be mainly described below.

The selection unit 212 according to the third embodiment selects a highest contrast frame as a mask image for a fluoroscopy roadmap. The display control unit 213 displays a fluoroscopy roadmap using the mask image selected by the selection unit 212.

Figure 12:
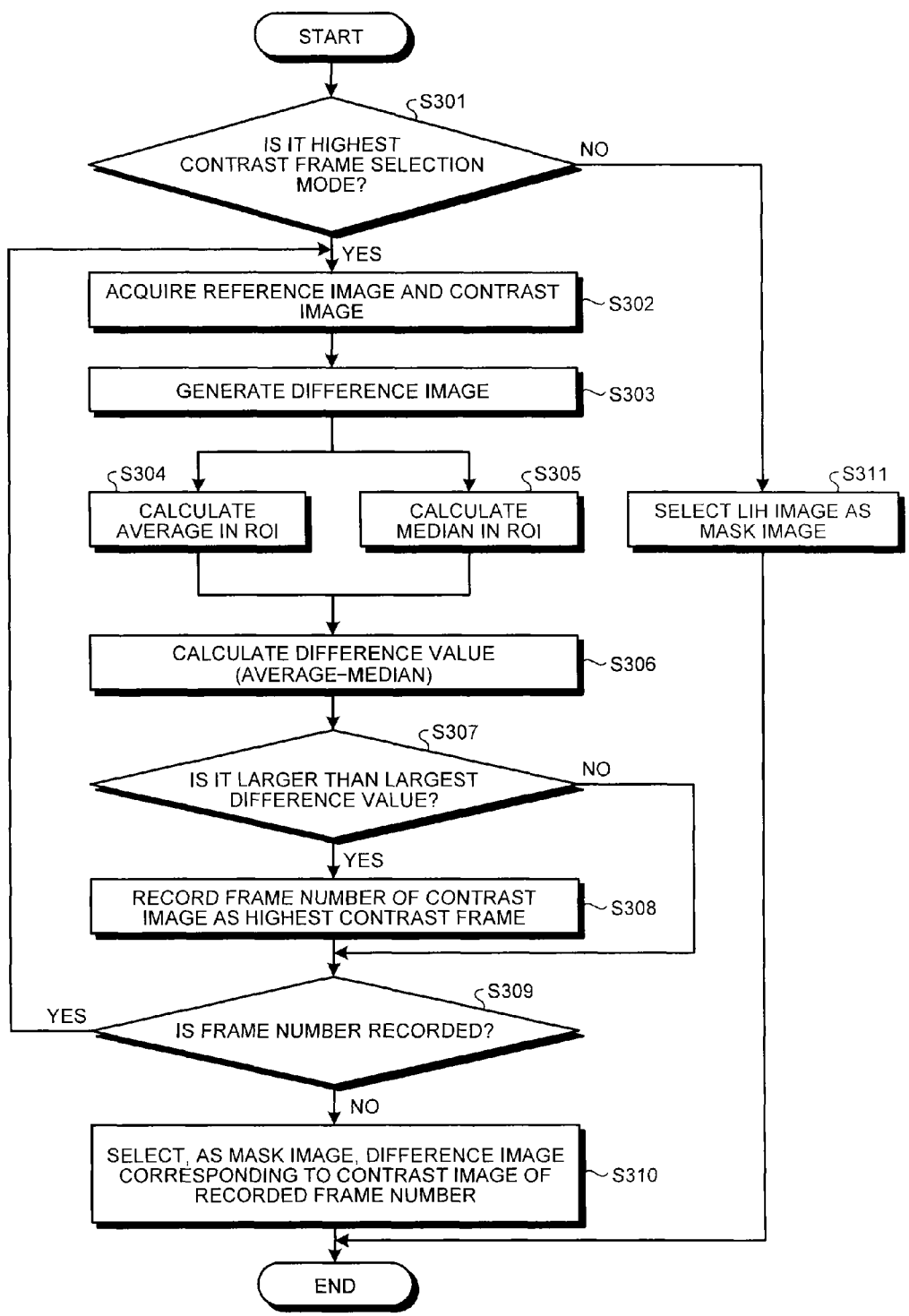
FIG. 12 is a flowchart of a processing procedure taken by the X-ray diagnosis apparatus according to a third embodiment.

FIG. 12 is a flowchart of a processing procedure taken by the X-ray diagnosis apparatus 100 according to the third embodiment. FIG. 12 shows the processing performed after a contrast material is injected and X-ray images are captured chronologically. FIG. 12 shows a case where an average and a median of pixel values of pixels of an ROI are calculated. Furthermore, FIG. 12 shows the case where difference values of respective frames are not averaged and are calculated separately.

As shown in FIG. 12, in the X-ray diagnosis apparatus 100 according to the third embodiment, when it is a highest contrast frame selection mode (YES at step S301), the image processing unit 26 acquires a reference image and a contrast image from the image data storage unit 25 (step S302) and generates a difference image (step S303). The calculation unit 211 calculates an average of pixel values of pixels in an ROI (step S304) and calculates a median of the pixel values of the pixels in the ROI (step S305).

Using the average and the median, the selection unit 212 then calculates a difference value (average−median) (step S306) and determines whether the calculated difference value is larger than the current largest difference value (step S307). When the selection unit 212 determines that the calculated difference value is larger than the current largest difference value (YES at step S307), the selection unit 212 records, as a highest contrast frame, the frame number of the contrast image of the frame (SUB image) for which the difference value is calculated (step S308).

On the other hand, when the selection unit 212 determines that the calculated difference value is not larger than the current largest difference value (NO step S307), the selection unit 212 does not record the frame number and goes to determination at step S309. The determination at step S309 is executed in the same manner as that according to the first embodiment. At step S309, when the selection unit 212 determines that the frame number is recorded (YES at step S309), the X-ray diagnosis apparatus 100 returns to step S302 and continues the processing.

On the other hand, when the selection unit 212 determines that the frame number is not recorded (NO at step S309), the selection unit 212 selects a difference image (SUB image) corresponding to the contrast image of the recorded frame number as a mask image (step S310). The display control unit 213 then causes the display unit 23 to display a fluoroscopy roadmap using the selected mask image. When it is not the highest contrast frame selection mode at step S301 (NO at step S301), the selection unit 212 may select, as a mask image, an LIH captured by an operator (step S311).

For the above-described processing procedure, the case where the difference values are compared according to the order of the frames to select a highest contrast frame has been described; however, embodiments are not limited to this. For example, the difference values may be calculated for all frames and the frame number of a frame representing the largest value among all of the calculated difference values may be recorded.

As described above, according to the third embodiment, the selection unit 212 selects a highest contrast image as an angiogram for a fluoroscopy roadmap. Accordingly, the X-ray diagnosis apparatus 100 according to the third embodiment can use, instead of the LIH mode of fluoroscopy roadmap, the angiogram captured when the blood vessels are most filled with the contrast material for the fluoroscopy roadmap. As described above, when an LIH image is used for a fluoroscopy roadmap, an LIH image is captured by turning off X-ray radiation at a time when it is determined that the blood vessels are filled with the contrast material during checks of fluoroscopic images on the monitor. For a site where the blood flows fast etc., however, it may be difficult to take the timing at which X-ray radiation is turned off. Even in such a case, the X-ray diagnosis apparatus 100 according to the third embodiment can assuredly generate a mask image captured when blood vessels are filled with the contrast material, which reduces the load on the technologist and thus makes it possible to increase the efficiency of manipulation.

Fourth Embodiment

For the above-described embodiment, the case where the selected highest contrast frame is displayed has been described. For a fourth embodiment, a case where a fact that a highest contrast frame is selected is used as a trigger for different processing will be described. Specifically, the X-ray diagnosis apparatus 100 according to the fourth embodiment uses the fact that a highest contrast frame is selected as a trigger for controlling X-ray radiation and controlling fluoroscopy roadmap display processing. The X-ray diagnosis apparatus 100 according to the fourth embodiment is different from the X-ray diagnosis apparatus 100 according to the first embodiment in the processing performed by the system control unit 21. The difference will be mainly described below.

For example, the system control unit 21 according to the fourth embodiment performs control to stop X-ray radiation on condition that the selection unit 212 selects a highest contrast frame. For example, to generate a mask image for a fluoroscopy roadmap, the system control unit 21 detects that the amount of the contrast material decreases after the highest contrast frame among multiple frames acquired sequentially and controls X-ray generators including the high-voltage generation unit 11 and the X-ray tube 12 to stop X-ray radiation.

For example, the system control unit 21 according to the fourth embodiment performs control to start fluoroscopy roadmap display processing on condition that the selection unit 212 selects a highest contrast frame. For example, the system control unit 21 detects that the amount of contrast material decreases after the highest contrast frame among multiple frames acquired sequentially and performs control to start the fluoroscopy roadmap sequence.

Figure 13:
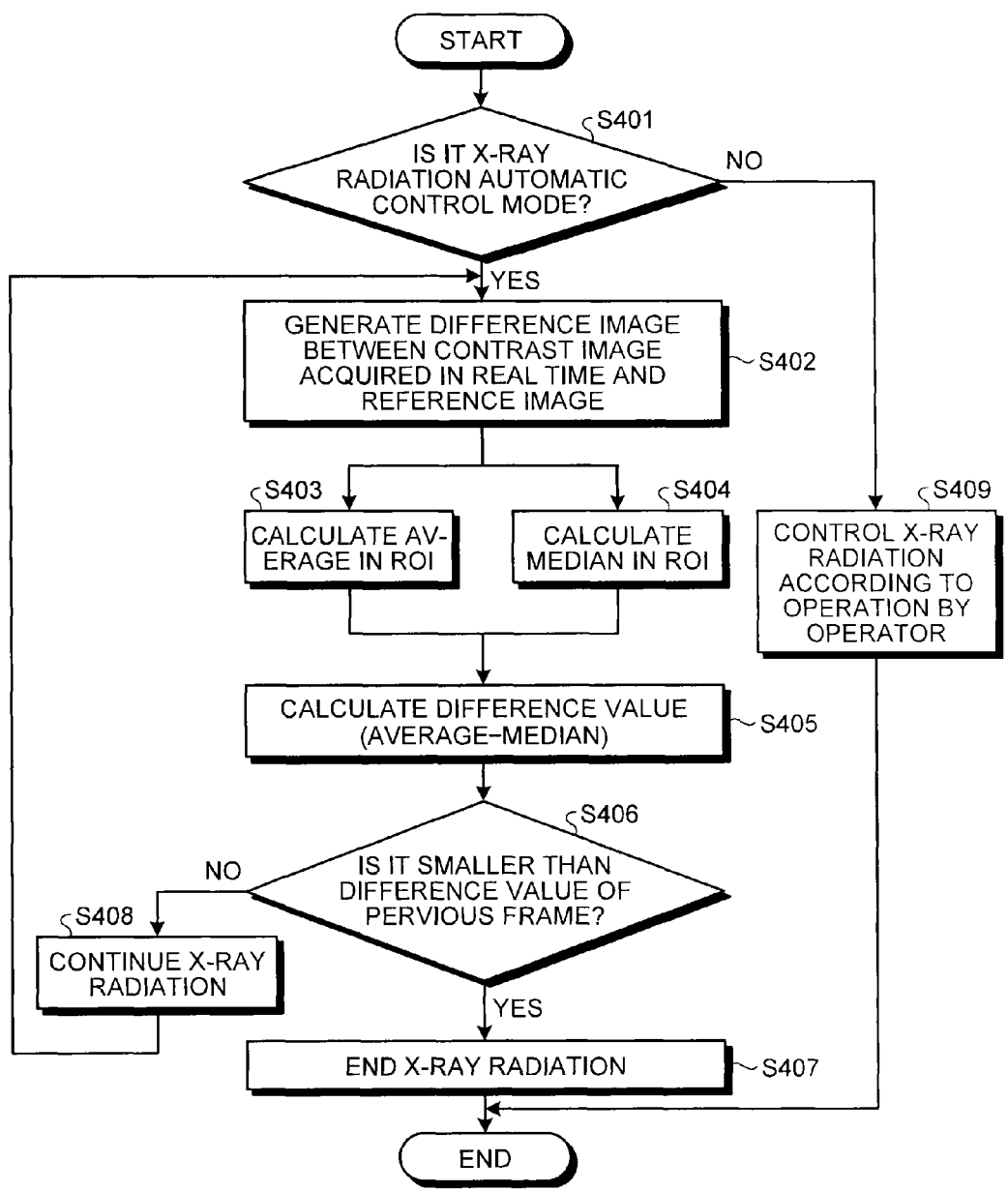
FIG. 13 is a flowchart of a processing procedure taken by the X-ray diagnosis apparatus according to a fourth embodiment.
Figure 14:
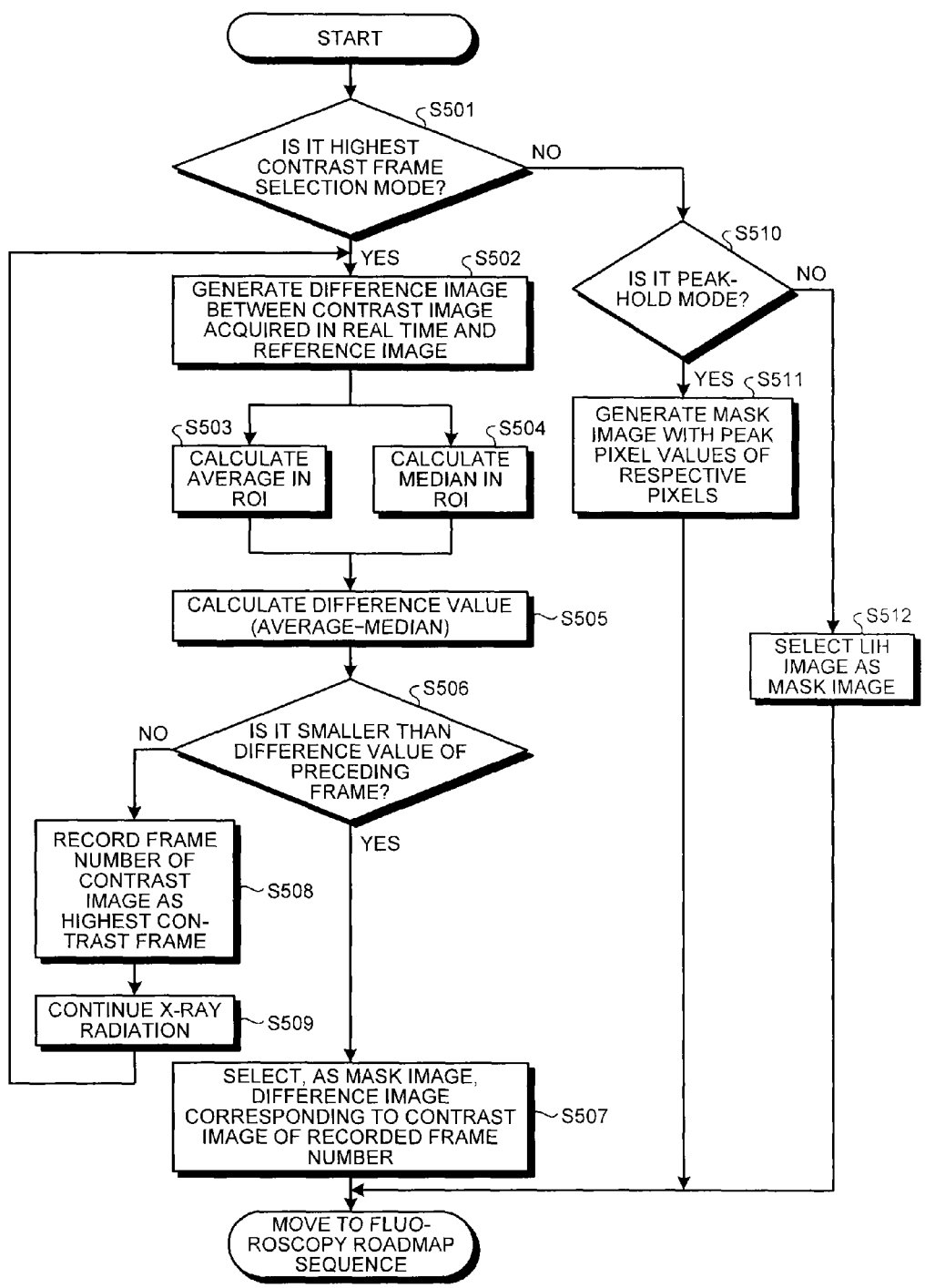
FIG. 14 is a flowchart of a processing procedure taken by the X-ray diagnosis apparatus according to the fourth embodiment.

With reference to FIGS. 13 and 14, the processing performed by the X-ray diagnosis apparatus 100 according to the fourth embodiment will be described. FIGS. 13 and 14 are flowcharts of the processing procedures taken by the X-ray diagnosis apparatus 100 according to the fourth embodiment. FIG. 13 shows a flowchart for controlling X-ray radiation. FIG. 14 shows a flowchart for controlling starting of fluoroscopy roadmap displaying. FIGS. 13 and 14 show cases where an average and a median of pixel values of pixels in an ROI are calculated. Furthermore, FIGS. 13 and 14 shows the cases where difference values of respective frames are not average and are calculated separately.

First, the case where X-ray radiation is controlled will be described. In this case, as shown in FIG. 13, in the X-ray diagnosis apparatus 100 according to the fourth embodiment, when it is an X-ray radiation automatic control mode (YES at step S401), the image processing unit 26 generates a difference image between a contrast image acquired in real time and a reference image (step S402). When the difference image is generated, the calculation unit 211 calculates an average of pixel values of pixels in an ROI (step S403), and calculates a median of the pixel values of the pixels in the ROI (step S404).

Using the average and the median, the selection unit 212 then calculates a difference value (average−median) (step S405) and determines whether the calculated difference value is smaller than the difference value of the preceding frame (step S406). When the selection unit 212 determines that the calculated difference value is larger than the difference value of the preceding frame (NO at step 3406), the system control unit 21 performs control to continue X-ray radiation (step S408).

On the other hand, when the selection unit 212 determines that the calculated difference value is smaller than the difference value of the preceding frame (YES at step 3406), the system control unit 21 ends the X-ray radiation (step S407). For the determination on whether the calculated difference value is smaller than the difference value of the preceding frame, for example, a fact that the difference value decreases even at once may be used as a condition Alternatively, in consideration of an increase or a decrease due to noise, a fact that the difference value decreases for successive multiple times may be used as a condition. For example, the system control unit 21 determines that the calculated difference value is smaller than the difference value of the preceding frame when the calculated difference value is smaller than the difference value of the preceding frame twice successively. At step S401, when it is not the X-ray radiation automatic control mode (NO at step S401), the system control unit 21 controls the X-ray radiation according to operations by the operator (step S409).

The case where starting of fluoroscopy roadmap display is controlled will be described here. In this case, as shown in FIG. 14, in the X-ray diagnosis apparatus 100 according to the fourth embodiment, when it is a highest contrast frame selection mode (YES at step 3501), the image processing unit 26 generates a difference image between a contrast image acquired in real time and a reference image (step S502). When the difference image is generated, the calculation unit 211 calculate an average of pixel values of pixels in an ROI (step S503), and calculates a median of the pixel values of the pixels in the ROI (step 3504).

Using the average and the median, the selection unit 212 then calculates a difference value (average−median) (step S505) and determines whether the calculated difference value is smaller than the difference value of the preceding frame (step S506). When the selection unit 212 determines that the calculated difference value is larger than the difference value of the preceding frame (NO at step S506), the selection unit 212 regards, as a highest contrast frame, the frame for which the difference value is calculated and records the frame number of the corresponding contrast image (step S508). The system control unit 21 then performs control to continue the X-ray radiation (step S509).

On the other hand, when the selection unit 212 determines that the calculated difference value is smaller than the difference value of the preceding frame (YES at step S506), the selection unit 212 selects the difference image corresponding to the contrast image of the recorded frame number as a mask image (step S507) and the system control unit 21 shifts the processing to the fluoroscopy roadmap sequence. The determination at step S506 is performed in the same manner as the determination at step S406 shown in FIG. 13.

At step S501, when it is not the highest contrast frame selection mode (NO at step S501), the system control unit 21 determines whether it is a peak-hold mode (step S510). When it is the peak-hold mod (YES at step 3510), the system control unit 21 performs control to generate a mask image by using the peak pixel value of each pixel for all frames of contrast images (step S511).

When it is not the peak-hold mode (NO at step S510), the system control unit 21 performs control to select an LIH image as a mask image (step S512). To the case shown in FIG. 14, a step of performing control to stop the X-ray radiation when a highest contrast frame is selected may be added. For example, when the determination at step S506 determines that the calculated difference value is smaller than the difference value of the preceding frame, the system control unit 21 stops the X-ray radiation.

As described above, according to the fourth embodiment, the system control unit 21 performs control to stop X-ray radiation on condition that the selection unit 212 selects a highest contrast frame. Accordingly, when acquiring X-ray images with a contrast material chronologically, unnecessary X-ray radiation can be prevented after the highest contrast frame, which makes it possible to reduce the exposure dose.

According to the fourth embodiment, the system control unit 21 performs control to start the fluoroscopy roadmap display processing on condition that the selection unit 212 selects a highest contrast frame. Accordingly, the X-ray diagnosis apparatus 100 according to the fourth embodiment simplifies various operations for LIH image capturing, which makes it possible to increase the efficiency of manipulation. For example, conventionally, when a mask image is generated in the LIH mode, a fluoroscopy roadmap sequence is started after a mask image is generated by turning off a foot switch for controlling X-ray radiation; however, without performing such processing, the X-ray diagnosis apparatus 100 according to the fourth embodiment can start the fluoroscopy roadmap sequence.

Fifth Embodiment

For the above-described embodiment, the case where the frame captured when the blood vessels are filled with the contrast material serves as the highest contrast frame has been described. For a fifth embodiment, a case here a frame is divided into multiple areas and a largest contrast frame is selected for each of the divided areas will be described. The X-ray diagnosis apparatus 100 according to the fifth embodiment is different from the X-ray diagnosis apparatus 100 according to the first embodiment in the processing performed by the calculation unit 211, the selection unit 212, and the display control unit 213. The difference will be mainly described below.

The calculation unit 211 according to the fifth embodiment divides an X-ray image into multiple areas and calculates an average and at least one of a median and a mode for each of the divided areas. For example, the calculation unit 211 calculates an average and at least any one of a median and a mode for each of the areas obtained by dividing an X-ray image in the direction approximately orthogonal to the direction in which the blood vessels contained in the X-ray image run. The above described areas may be set by the operator, or the calculation unit may detect the direction in which the blood vessels run and the X-ray image may be divided into multiple areas in the direction approximately orthogonal to the detected direction in which the blood vessels run.

The selection unit 212 according to the fifth embodiment selects a highest contrast frame per area. Specifically, the selection unit 212 compares the difference values of the frames per area and selects a highest contrast frame captured when the blood vessels are most filled with the contrast material for each of the areas. The display control unit 213 according to the fifth embodiment performs control to cause the display unit 23 to display a synthesis image synthesized from the largest contrast frames of the respective areas selected by the selection unit 212.

Figure 15:
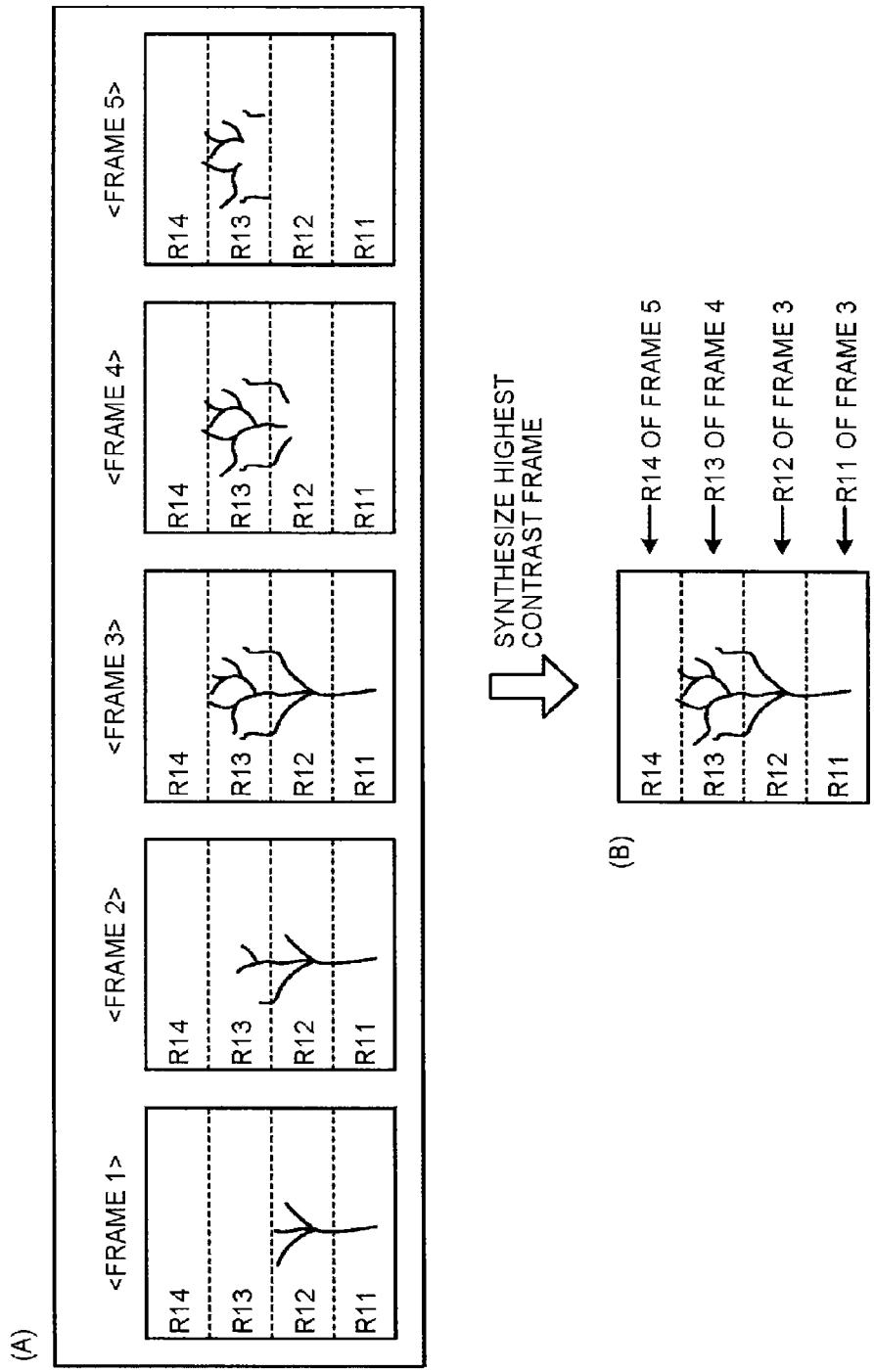
FIG. 15 is a diagram for explaining exemplary processing performed by an X-ray diagnosis apparatus according to a fifth embodiment.

FIG. 15 is a diagram for explaining exemplary processing performed by the X-ray diagnosis apparatus 100 according to the fifth embodiment. FIG. 15 shows a case where highest contrast frames are selected from SUB images of Frames 1 to 5 to synthesize a synthesis image. Furthermore, FIG. 5 illustrates a case where highest contrast frames are selected using difference values each between an average and a median of pixel values.

For example, as shown in (A) in FIG. 15, the calculation unit 211 divides each frame into four areas of R11 to R14 in a direction approximately orthogonal to the direction in which the blood vessels run (or in a direction crossing the direction in which the blood vessels run) and calculates an average and a median of the pixel values for each the areas per frame. For example, the calculation unit 211 calculates an average and a median of the pixel values of each of the areas R11 to R14 of Frame 1. In the same manner, for each of Frames 2 to 5, the calculation unit 211 calculates an average and a median of the pixel values of each of the areas R11 to R14.

The selection unit 212 calculates a difference value for each area of each frame, compares the calculated difference values of the respective frames in the same area, and selects a frame with the largest difference value as a highest contrast frame for the compared area. For example, the selection unit 212 compares the difference values of the area R11 shown in (A) in FIG. 15 among Frames 1 to 5 and selects Frame 3 with the largest difference value as a highest contrast frame for the area R11. In the same manner, the selection unit 212 compares the difference values of the areas R12 to R14 among the frames and selects a highest contrast frame of each of the areas. For example, as shown in (B) in FIG. 15, the selection unit 212 selects Frame 3 as a highest contrast frame for the area R12, selects Frame 4 as a highest contrast frame for the area R13, and selects Frame 5 as a highest contrast frame for the area R14.

The display control unit 213 generates a synthesis image synthesized from the selected highest contrast frames for the respective areas and performs control to display the synthesis image on the display unit 23. For example, as shown in (B) in FIG. 15, the display control unit 213 synthesizes the synthesis image in which the area R11 of Frame 3 is arranged as the area R11, the area R12 of Frame 3 is arranged for the area R12, the area R13 of Frame 4 is arranged for the area R13, and the area R14 of Frame 5 is arranged for the area R14 and performs control to display the synthesis image on the display unit 23.

Figure 16:
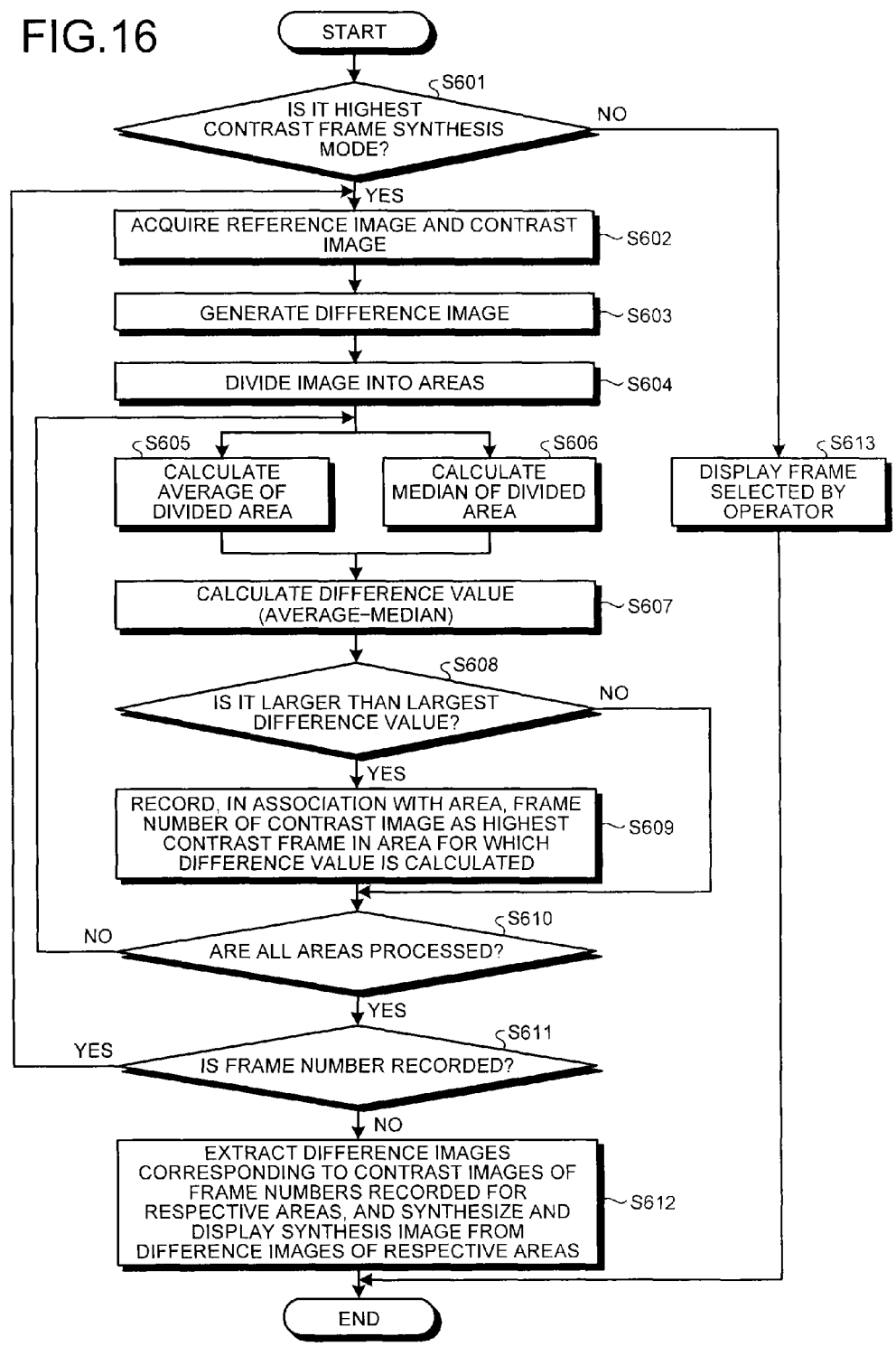
FIG. 16 is a flowchart of a processing procedure taken by the X-ray diagnosis apparatus according to the fifth embodiment.

With reference to FIG. 16, the processing performed by the X-ray diagnosis apparatus 100 according to the fifth embodiment will be described. FIG. 16 is a flowchart of a processing procedure taken by the X-ray diagnosis apparatus 100 according to the fifth embodiment. FIG. 16 shows processing performed after a contrast material is injected and X-ray images are captured chronologically. FIG. 16 shows a case where an average and a median of pixel values of pixels in an ROI are calculated. Furthermore, FIG. 16 shows the case where difference values of the respective frames are not averaged and are calculated separately.

As shown in FIG. 16, in the X-ray diagnosis apparatus 100 according to the fifth embodiment, when it is a highest contrast frame synthesis mode (YES at step S601), the image processing unit 26 acquires a reference image and a contrast image from the image data storage unit 25 (step S602) and generates a difference image (step S603). The calculation unit 211 divides the difference image into multiple areas (step S604), calculates an average of pixel values of pixels of each of the divided areas (step S605) and calculates a median of the pixel values of the pixels in each of the divided areas (step S606).

Using the average and the medias that are calculated by the calculation unit 211, the selection unit 212 then calculates a difference value (average−median) of an area (step S607) and determines whether the calculated difference value is larger than the current largest difference value (step S608). When the selection unit 212 determines that the calculated difference value is larger than the current largest difference value (YES at step S608), the selection unit 212 records, as a highest contrast frame of the area for which the difference value is calculated, the frame number of the contrast image of the frame (SUB image) for which the difference value is calculated (step S609).

On the other hand, when the selection unit 212 determines that the calculated difference value is not larger than the current largest difference value (NO step S608), the selection unit 212 does not record the correspondence between the frame number and the area and goes to determination at step S610. After recording the frame number in association with the area because the calculated difference value is larger than the current largest difference value (YES at step S608) or after determining that the calculated difference value is not larger than the current largest difference value, the selection unit 212 determines whether the processing is performed on all the areas contained in the frame (step S610).

When the selection unit 212 determines that the processing is performed on not all the areas contained in the frame (NO at step S610), the calculation unit 211 returns to step S605 and continues the processing on unprocessed areas. On the other hand, when the selection unit 212 determines that the processing is performed on all the areas contained in the frame (YES at step S610), the selection unit 212 determines whether the frame number is recorded (step S611). The determination at step S611 is performed in the same manner as that at step S109 shown in FIG. 10. When, at step S611, the selection unit 212 determines that the frame number is recorded (YES at step S611), the X-ray diagnosis apparatus 100 returns to step S602 and continues the processing.

On the other hand, when the selection unit 212 determines that the frame number is not recorded (NO at step S611), the display control unit 213 extracts difference image (SUB images) corresponding to the contrast image of the frame number recorded per area and causes the display unit 23 to display a synthesis image synthesized from the difference images of the respective areas (step S612). When, at step S601, it is not the highest contrast frame synthesis mode (NO at step S601), the display control unit 213 causes the display unit 23 to display a SUB image of a frame selected by the operator (step S613).

For the processing procedure, the case has been described where difference values are compared according to the order of frames to select a highest contrast frame; however, embodiments are not limited to this. For example, difference values may be generated for all frames and the frame number representing the largest value among all of the calculated difference values may be recorded in association with the area.

As described above, according to the fifth embodiment, the calculation unit 211 divides an X-ray image into multiple areas and calculates an average and at least any one of a median and a mode for each of the divided areas. The selection unit 212 selects a highest contrast image per area. The display control unit 213 performs control to cause the display unit 23 to display a synthesis image synthesized from the highest contrast images for the respective areas selected by the selection unit 212. Accordingly, the X-ray diagnosis apparatus 100 according to the fifth embodiment makes it possible to generate a synthesis image most depicting blood vessels by using the multiple X-ray images acquired with the contrast material chronologically.

According to the fifth embodiment, the calculation unit 211 calculates an average and at least any one of a median and a mode for each of the areas obtained by dividing the X-ray image in the direction approximately orthogonal to the direction in which the blood vessels contained in the X-ray image run. Accordingly, the X-ray diagnosis apparatus 100 according to the fifth embodiment makes it possible to select an image captured when the blood vessels are most filled with the contrast material for each blood vessel area.

Sixth Embodiment

For the above-described embodiment, the case where the highest contrast image is selected from the multiple X-ray images acquired with the contrast material chronologically. For a sixth embodiment, a case where a medical device is detected will be described. The X-ray diagnosis apparatus 100 according to the sixth embodiment is different from the X-ray diagnosis apparatus 100 according to the first embodiment in the processing performed by the selection unit 212. The difference will be mainly described below.

Figure 17:
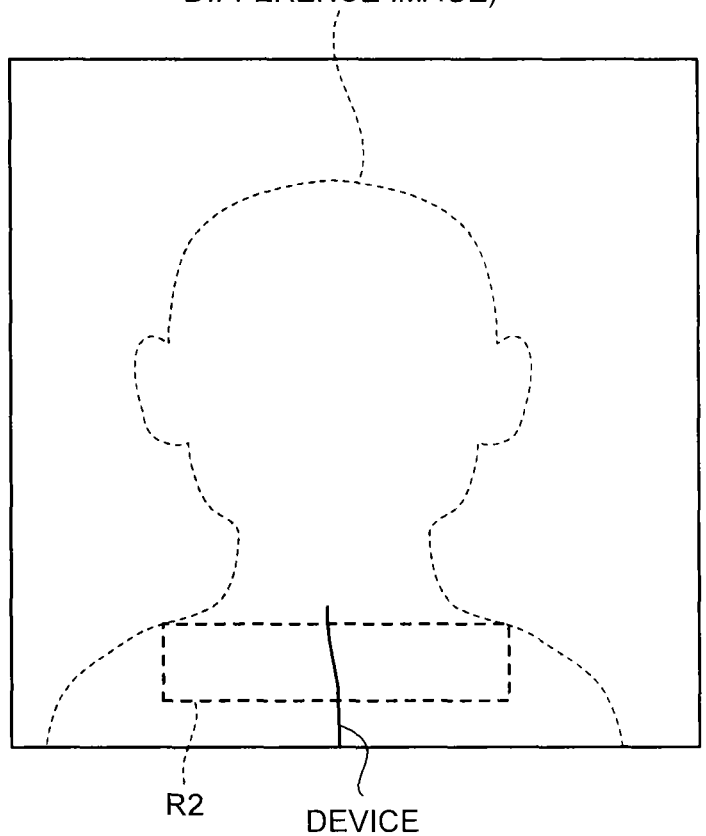
FIG. 17 is a diagram for explaining exemplary processing performed by an X-ray diagnosis apparatus according to a sixth embodiment.

The selection unit 212 according to the sixth embodiment selects, as an image depicting a medical device, an X-ray image in which the difference between the average and the median or the mode, the ratio between the average and the median or the mode, or the number of pixels representing the value equal to or larger than the average, the median, or the mode exceeds a given threshold. FIG. 17 is a diagram for explaining exemplary processing performed by the X-ray diagnosis apparatus 100 according to the sixth embodiment. FIG. 17 illustrates an example where a medical device is inserted into the head of a subject. Furthermore, FIG. 17 further illustrates the case where the medical device is detected by using a difference value between the average and the median of the pixel values.

To detect the medical device, first, an ROI is set at the position where the medical device is inserted. For example, when the medical device is inserted into the head, as shown in FIG. 17, an ROI "R2" is set below the neck of the subject. The ROI "R2" may be set by the operator or set according to the position of the subject upon image capturing. FIG. 17 shows the outline of the subject for the explanation; however, practically, the outline is not shown on the image because it is a difference image.

Once the ROI "R2" is set as described above, the calculation unit 211 calculates an average and a median of pixel values of pixels contained in the ROI "R2". The selection unit 212 calculates the difference value in the ROI "R2" and, when the calculated difference value exceeds a given threshold, determines that the image shows that the medical device is inserted into the ROI "R2". In other words, when the medical device is gradually inserted into the ROI "R2" and the average of the pixel values in the ROI "R2" gradually increases, the selection unit 212 detects the medical device by extracting the frame at the time when the medical device is inserted to some extent.

Figure 18:
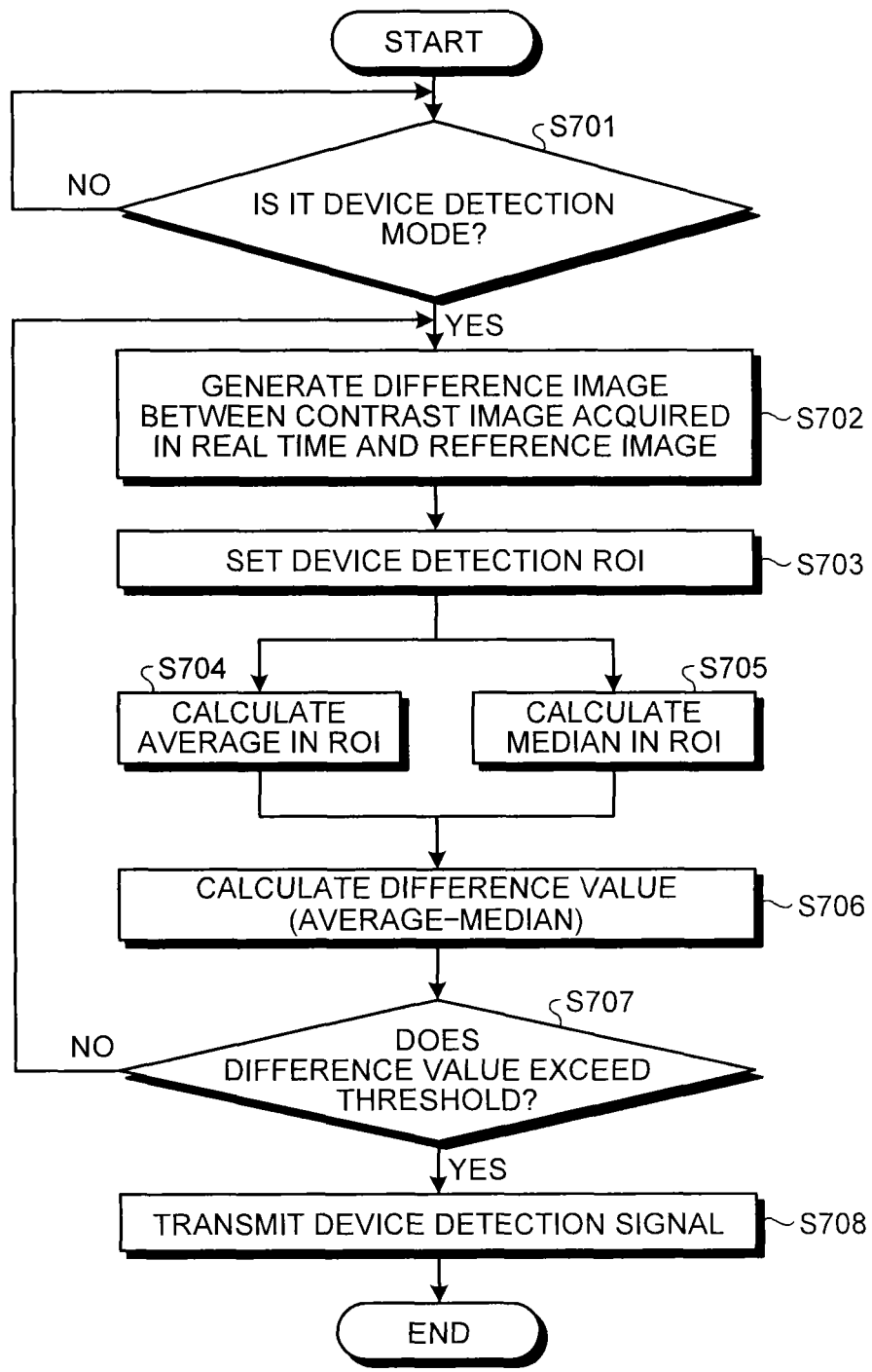
FIG. 18 is a flowchart of a processing procedure taken by the X-ray diagnosis apparatus according to the sixth embodiment.

With reference to FIG. 18, the processing performed by the X-ray diagnosis apparatus 100 according to the sixth embodiment will be described. FIG. 18 is a flowchart of a processing procedure taken by the X-ray diagnosis apparatus 100 according to the sixth embodiment. FIG. 18 shows the case where an average and a median of pixel values of pixels in an ROI are calculated. Furthermore, FIG. 18 shows the case here the difference values of the respective frames are not average and are calculated separately.

As shown in FIG. 18, in the X-ray diagnosis apparatus 100 according to the sixth embodiment, when it is a device detection mode (YES at step S701), the image processing unit 26 generates a difference image between a contrast image acquired real time and a reference image (step S702). When the difference image is generated, the calculation unit 211 sets a device detection ROI (step S703), calculates an average of the pixel values of the pixels in the ROI (step S704), and calculates a median of the pixel values of the pixels in the ROI (step S705).

Using the average and the median, the selection unit. 212 then calculates a difference value (average−median) (step S706) and determines whether the calculated difference value exceeds a threshold (step S707). When the selection unit 212 determines that the calculated difference value exceeds the threshold (YES at step S707), the selection unit 212 transmits a device detection signal to the system control unit 21 (step S708). On the other hand, when the selection unit 212 determines that the calculated difference value does not exceed the threshold (NO at step S707), the X-ray diagnosis apparatus 100 returns to step S702 and continues the real time processing. When, at step S701, it is not the device detection mode (NO at step S701), the X-ray diagnosis apparatus 100 enters a standby state.

The above-described detection of the medical device can be used in variety. For example, it is possible to set a low dose before the device is detected and may be switched to a proper dose after the device is detected. In other words, in a case where the selection unit 212 selects an image depicting the medical device, the system control unit 21 controls X-ray radiation such that the dose before the selection of the image is lower than the dose after the selection of the image. For example, the system control unit 21 controls the X-ray generator including the high-voltage generation unit 11 and the X-ray tube 12 to radiate x-rays at a low dose and, upon receiving a device detection signal from the selection unit 212, controls the X-ray generator to radiate X-rays at a proper dose.

For example, the frame rate may be controlled before and after the medical device is detected. For example, when the selection unit 212 selects an image depicting the medical device, the system control unit 21 controls image generation such that the frame rate before the image selection is lower than that after the image selection. For example, the system control unit 21 first performs control to acquire images at a low frame rate and, upon receiving a device detection signal from the selection unit 212, performs control to acquire images at a high frame rate. The above-described control on the dose and on the frame rate may be arbitrarily set by the operator.

As described above, according to the sixth embodiment, the selection unit 212 selects an X-ray image in which the difference between the average and the median or the mode exceeds the given threshold as an image depicting the medical device. Accordingly, the X-ray diagnosis apparatus 100 according to the sixth embodiment can accurately detect the medical device, which increases the efficiency of manipulation.

Seventh Embodiment

The first to sixth embodiments have been described above, the embodiments may be implemented in various different forms other than the foregoing first to six embodiments.

For the first to sixth embodiments, the case where the highest contrast frame acquired when the contrast material is injected into the blood vessels is selected has been described; however, embodiments are not limited to this. For example, a highest contrast frame acquired when a contrast material (barium) passes through the esophagus.

For the first to sixth embodiments, the case where the largest contrast frame or the medical device is detected according to the difference value between the average and the median of the pixel values have been described; however, embodiments are not limited to this. For example, the highest contrast frame may be selected or the medical device may be detected according to the difference value between the average and the mode of the pixel values.

According to, instead of the difference value between the average and the mode of the pixel values, the ratio between the average and the median of the pixel values, the highest contrast frame or the medical device may be detected. In such a case, for example, the selection unit 212 selects, as the highest contrast frame or a frame depicting the medical device, a frame with the largest "ratio" obtained by "dividing the average by the median" in the ROI.

Alternatively, the highest contrast frame may be selected or the medical device may be detected according to the number of pixels each representing a value equal to or higher than the average, the median, or the mode. In such a case, for example, the selection unit 212 selects a frame with the largest number of pixels each representing a value equal to or larger than the average, the median, or the mode as a highest contrast frame or a frame depicting the medical device. The case using the median as mentioned above will be exemplified below. Because the number of pixels each representing a value equal to or larger than the median increases, a frame with the largest number of pixels each representing a value equal to or larger than the median serves as a highest contrast frame. Thus, for example, the selection unit 212 selects, as a highest contrast frame, a frame with the largest ratio of the number of pixels each representing a pixel value equal to or larger than the median in the ROI with respect to the total number of pixels in the ROI.

For the above-describe example, the case where the number of pixels each representing a value equal to or larger than the median has been described. Alternatively, the number of pixels each representing a value equal to or smaller than the median may be used. In such a case, the selection unit 212 selects a frame with the smallest ratio as a highest contrast frame. Alternatively, the number of pixels each representing a value equal to or larger than, or equal to or smaller than, the average or the mode may be measured.

For the first to sixth embodiments, the case where the values calculated from the respective frames are used for the difference values of the respective frames are directly used has been described; however, embodiments are not limited to this. For example, difference values of multiple frames may be averaged.

For the above-described first to sixth embodiments, the case has been described where the highest contrast frame is selected (extracted) or the medical device is detected according to the difference value between the average and the median of the pixel values, the ratio between the average and the median of the pixel values, or the number of pixels each representing a value equal to or larger than the average, the median, or the mode; however, embodiments are not limited to this. For example, the highest contrast frame may be selected (extracted) or the medical device may be detected by using the degree of distortion of each frame with respect to the normal distribution of the histogram of the pixel values.

Figure 19:
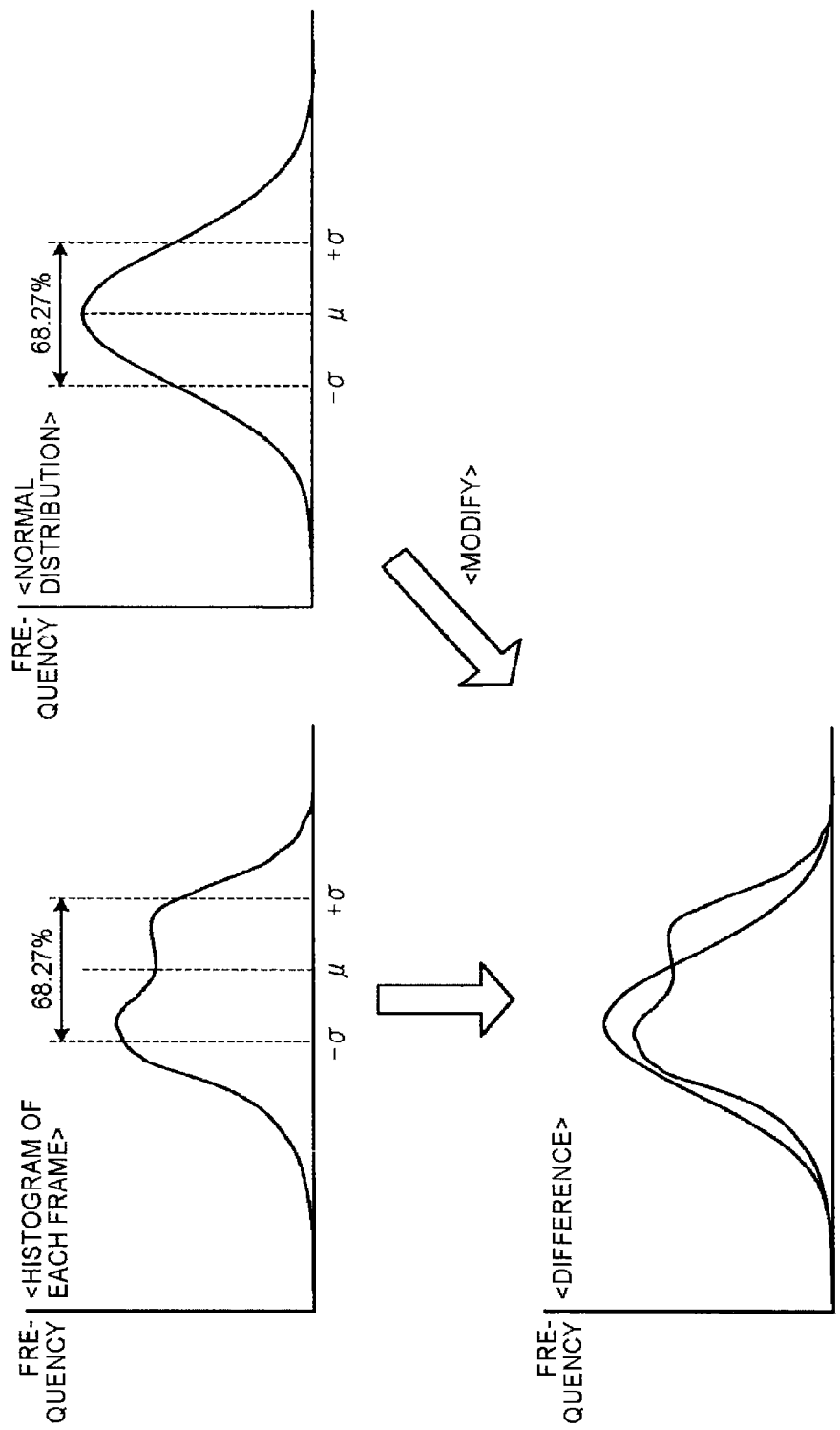
FIG. 19 is a diagram for explaining exemplary image selection by a selection unit according to a seventh embodiment.
Figure 20:
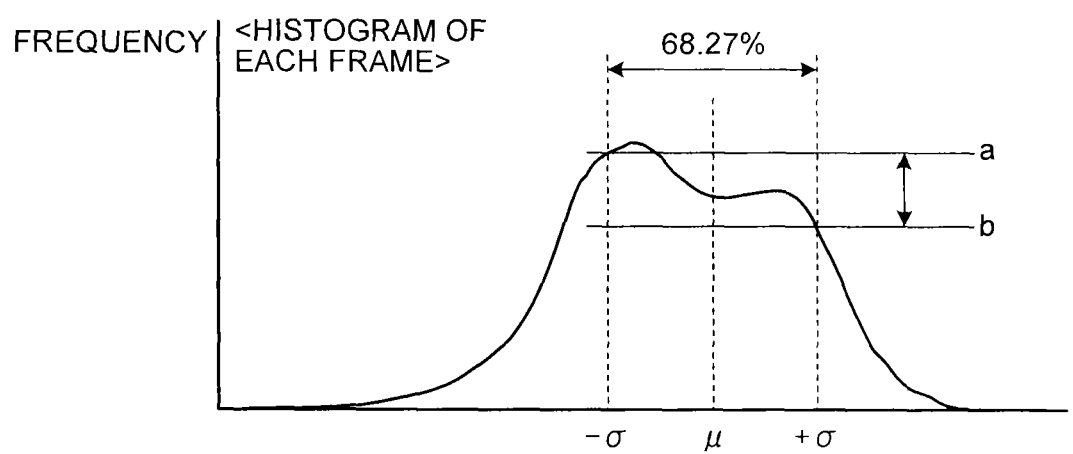
FIG. 20 is a diagram for explaining exemplary image selection by the selection unit according to the seventh embodiment.

Specifically, the calculation unit 211 according to the seventh embodiment calculates a distribution of pixel values for each of multiple X-ray images acquired chronologically. The selection unit 212 according to the seventh embodiment selects an X-ray image with a high degree of distortion of the distribution of pixel values with respect to the normal distribution. In other words, the calculation unit 211 generates histograms for the respective frames and the selection unit 212 analyzes the histograms of the generated respective frames according to the normal distribution that serves as a reference and selects an X-ray image with a high degree of distortion of the histogram. The selection unit 212 uses, as the degree of distortion of the histogram of pixels with respect to the normal distribution, a difference between the normal distribution and the histogram of pixel values, or the difference in the frequency according to the standard deviation of the histogram of pixel values. A case where a difference between a normal distribution and a histogram of pixel values is used and a case where a difference in the frequency according to a standard deviation of a histogram of pixel values will be described with reference to FIGS. 19 and 20. FIGS. 19 and 20 are diagrams for explaining exemplary image selection by the selection unit 212 according to the seventh embodiment.

First, the case where a difference between a normal distribution and a histogram of pixel values are used will be described. As described above, a histogram of difference values of a SUB image represents a normal distribution but does not represents the normal distribution when a contrast material flows into and the average of pixel values increases. In other words, an increase in the area into which the contrast material flows into gradually increases the number of pixels having high pixel values and thus increases the average, which increases the degree of distortion with respect to the normal distribution. For this reason, for example, the selection unit 212 calculates the difference between the histogram of each frame and the normal distribution that serves as the reference and selects a frame with the largest calculated difference as a highest contrast frame.

To perform the above-described processing, the selection unit 212 performs processing of approximating the scales of the histogram of each frame and the scale of the normal distribution serving as the reference. For example, as shown in FIG. 19, the selection unit 212 extracts one frame (e.g., the first frame) from the histograms of the respective frames calculated by the calculation unit 211 and extracts the average "µ" of the histograms of the extracted frames and a standard deviation "±σ" containing the data of "68.27%". The selection unit 212 further extracts an average "µ" and a standard deviation "±σ" of a pre-set normal distribution serving as a reference. The selection unit 212 then approximates the scale of the histogram of the frame and the scale of the normal distribution by using the averages "µ" and the normal deviations "±σ" that are extracted from the histogram of the frame and the normal distribution.

For example, the selection unit 212 modifies the normal distribution to such that make the width from "−σ" to "+σ" in the normal distribution equals to the width from "−σ" to "+σ" in the histogram. The selection unit 212 further modifies the normal distribution such that the height of "±σ" in the normal distribution equals to the average of the height of "−σ" and the height of "+σ" in the histogram. The selection unit 212 then calculates a difference between the modified normal distribution and each histogram and selects a frame with the largest difference as a highest contrast frame. For example, the selection unit 212 calculates, per frame, the value obtained by squaring the difference between the histogram of the frame and the modified normal distribution and selects a frame with the largest value as a highest contrast frame. Alternatively, the selection unit 212 calculates, per frame, a value obtained by squaring the difference between the histogram of the frame and the modified normal distribution and selects a frame with the largest value as a frame depicting the medical device.

The case where a difference in the frequency according to a standard deviation of a histogram of pixel values is used will be described next. As described above, an increase in the area into which the contrast material flows into gradually increases the number of pixels having high pixel values and thus increases the average, which increases the degree of distortion with respect to the normal distribution. In other words, in the normal distribution, the height of "−σ" and the height of "+σ" are equal to each other; however, it is assumed that, as the area into which the contrast material flows increases, the difference between the height of "−σ" and the height of "+σ" in the histogram increases. For this reason, the selection unit 212 calculates the differences each between the height of "−σ" and the height of "+σ" in the histograms of the respective frames and selects a frame with the largest difference as a highest contrast frame.

For example, as shown in FIG. 20, the selection unit 212 calculates, per frame, a difference between the height (frequency) "a" of "−σ" and the height (frequency) "b" of "+σ". The selection unit 212 selects a frame with the largest difference as a highest contrast frame. The selection unit 212 may also select a frame with the largest difference as a frame depicting the medical device. As described above, by using the difference the height of "−σ" and the height of "+σ" without using the normal distribution, it is possible to select a highest contrast frame or select a frame depicting the medical device.

In the above-described example, the case has been described where, as for the difference between the histogram of each frame and the normal distribution or the difference between the height of "−σ" and the height of "+σ" in the histogram, the values calculated from the respective frames are directly used; however, embodiments are not limited to this. For example, the values of multiple frames may be averaged.

As described above, the X-ray diagnosis apparatus according to at least one of the embodiments makes it possible to increase the efficiency of manipulation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus, comprising:
    an X-ray tube configured to generate X-rays;
    an X-ray detector configured to detect the X-rays that have passed through a subject; and
    processing circuitry configured to
        calculate, for each X-ray image of a plurality of X-ray images that are acquired chronologically, an average of pixel values of the X-ray image, and a reference value, based on the pixel values of the X-ray image, and
        select, from the plurality of X-ray images, an X-ray image with a largest difference between the average and the reference value, an X-ray image with a highest ratio between the average and the reference value, or an X-ray image with a largest number of pixels, each representing a value equal to or larger than the average or the reference value.

2. The X-ray diagnosis apparatus according to claim 1, wherein the reference value calculated by the processing circuitry is a median or a mode of the pixel values of the X-ray image.

3. The X-ray diagnosis apparatus according to claim 1, wherein the processing circuitry is further configured to
    calculate the average and the reference value based on the pixel values for a plurality of difference images obtained by subtracting the background from each of the X-ray images that are acquired with a contrast material chronologically, and select, as contrast images in which the contrast obtained with the contrast material is proper, the X-ray image with the largest difference between the average and the reference value, the X-ray image with the highest ratio between the average and the reference value, and the X-ray image with the largest number of pixels each representing the value equal to or larger than the average or the reference value.

4. The X-ray diagnosis apparatus according to claim 3, wherein the processing circuitry is further configured to select the contrast image as a blood vessel image for a fluoroscopy roadmap.

5. The X-ray diagnosis apparatus according to claim 4, wherein the processing circuitry is further configured to perform control to start processing of displaying the fluoroscopy roadmap, when the contrast image is selected.

6. The X-ray diagnosis apparatus according to claim 3, wherein the processing circuitry is further configured to perform control to stop X-ray radiation, when the contrast image is selected.

7. The X-ray diagnosis apparatus according to claim 3, wherein the processing circuitry is further configured to perform control to cause a display to display the selected contrast image.

8. The X-ray diagnosis apparatus according to claim 7, wherein the processing circuitry is further configured to
divide the X-ray image into a plurality of areas and calculate, for each of the divided areas, the average and the reference value based on the pixel values, and
extract a contrast image for each of the areas and perform control to cause the display to display a synthesis image synthesized from the contrast images selected for the respective areas.

9. The X-ray diagnosis apparatus according to claim 8, wherein the processing circuitry is further configured to calculate the average and the reference value based on the pixel values for each of the areas divided in a direction approximately orthogonal to a direction in which blood vessels are contained in the X-ray image.

10. The X-ray diagnosis apparatus according to claim 1, wherein the processing circuitry is further configured to use an average of X-ray images that are sequentially captured as the difference between the average and the reference value, the ratio between the average and the reference value, or the number of pixels each representing a value equal to or larger than the average or the reference value.

11. The X-ray diagnosis apparatus according to claim 1, wherein the processing circuitry is further configured to select, as an image including a medical device, an X-ray image in which a difference between the average and the reference value, the ratio between the average and the reference value, or the number of pixels each representing a value equal to or larger than the average or the reference value exceeds a given threshold.

12. The X-ray diagnosis apparatus according to claim 11, wherein, when an image including the medical device is selected, the processing circuitry is further configured to control X-ray radiation such that a dose before selection of the image is lower than that after selection of the image.

13. The X-ray diagnosis apparatus according to claim 11, wherein, when an image including the medical device is selected, the processing circuitry is further configured to control generation of images such that a frame rate before selection of the image is lower than a frame rate after selection of the image.

14. An X-ray diagnosis apparatus, comprising:
an X-ray tube configured to generate X-rays;
an X-ray detector configured to detect the X-rays that have passed through a subject; and
processing circuitry configured to
calculate, for each of a plurality of X-ray images that are acquired chronologically, a distribution of pixel values, and
select, from the plurality of X-ray images, an X-ray image in which a degree of deviation of the distribution of the pixel values with respect to a normal distribution is high.

15. The X-ray diagnosis apparatus according to claim 14, wherein the processing circuitry is further configured to use, as the degree of deviation of the distribution of the pixel values with respect to the normal distribution, a difference between the normal distribution and the distribution of the pixel values, or a difference in a frequency according to a standard deviation of the distribution of the pixel values.

16. The X-ray diagnosis apparatus according to claim 14, wherein the processing circuitry is further configured to
calculate the distribution of the pixel values for multiple difference images obtained by subtracting a background from each of the X-ray images that are acquired with a contrast material chronologically, and
select, as a contrast image with a proper contrast obtained with the contrast material, an X-ray image with a high degree of deviation of the distribution of the pixel values with respect to a normal distribution.

17. The X-ray diagnosis apparatus according to claim 16, wherein the processing circuitry is further configured to select the contrast image as an blood vessel image for a fluoroscopy roadmap.

18. The X-ray diagnosis apparatus according to claim 17, wherein the processing circuitry is further configured to perform control to start processing of displaying the fluoroscopy roadmap, when the contrast image is selected.

19. The X-ray diagnosis apparatus according to claim 16, wherein the processing circuitry is further configured to perform control to stop X-ray radiation, when the contrast image is selected.

20. The X-ray diagnosis apparatus according to claim 16, wherein the processing circuitry is further configured to perform control to cause a display to display the selected contrast image.

21. The X-ray diagnosis apparatus according to claim 20, wherein the processing circuitry is further configured to
divide the X-ray image into a plurality of areas and calculate the distribution of the pixel values for each of the divided areas, and
select the contrast image from each of the areas and perform control to cause the display to display a synthesis image synthesized from the contrast images selected from the respective areas.

22. The X-ray diagnosis apparatus according to claim 21, wherein the processing circuitry is further configured to calculate the distribution of the pixel values for each of the areas divided in a direction approximately orthogonal to a direction in which blood vessels are contained in the X-ray image.

23. The X-ray diagnosis apparatus according to claim 14, wherein the processing circuitry is further configured to use an average of X-ray images that are sequentially captured as the degree of distortion of the distribution of pixel values with respect to the normal distribution.

24. The X-ray diagnosis apparatus according to claim 14, wherein the processing circuitry is further configured to select, as an image including a medical device, an X-ray image in which the degree of deviation of the distribution of the pixel values with respect to the normal distribution exceeds a given threshold.

25. The X-ray diagnosis apparatus according to claim 24, wherein, when an image including the medical device is selected, the processing circuitry is further configured to control X-ray radiation such that a dose before selection of the image is lower than that after selection of the image.

26. The X-ray diagnosis apparatus according to claim 1, wherein, when an image including the medical device is selected, the processing circuitry is further configured to control generation of images such that a frame rate before selection of the image is lower than a frame rate after selection of the image.

* * * * *